United States Patent
Badylak et al.

(10) Patent No.: US 12,383,243 B2
(45) Date of Patent: Aug. 12, 2025

(54) EXTRACELLULAR MATRIX (ECM) HYDROGEL AS A SUBMUCOSAL FLUID CUSHION

(71) Applicant: University of Pittsburgh—Of the Commonwealth System of Higher Education, Pittsburgh, PA (US)

(72) Inventors: Stephen Francis Badylak, West Lafayette, IN (US); Lindsey Tamiko Saldin, El Segundo, CA (US); Juan Diego Naranjo Gutierrez, Manizales (CO)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 594 days.

(21) Appl. No.: 17/581,591

(22) Filed: Jan. 21, 2022

(65) Prior Publication Data

US 2022/0354473 A1    Nov. 10, 2022

Related U.S. Application Data

(63) Continuation of application No. 17/254,040, filed as application No. PCT/US2019/038317 on Jun. 20, 2019, now abandoned.

(60) Provisional application No. 62/688,198, filed on Jun. 21, 2018.

(51) Int. Cl.
| | |
|---|---|
| *A61B 17/00* | (2006.01) |
| *A61L 27/36* | (2006.01) |
| *A61L 27/52* | (2006.01) |

(52) U.S. Cl.
CPC .... *A61B 17/00234* (2013.01); *A61L 27/3633* (2013.01); *A61L 27/3687* (2013.01); *A61L 27/52* (2013.01); *A61B 2017/00269* (2013.01); *A61L 2400/06* (2013.01)

(58) Field of Classification Search
CPC .... A61B 17/00234; A61B 2017/00269; A61L 27/3633; A61L 27/3687; A61L 27/52; A61L 2400/06
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 4,978,668 A | 12/1990 | Babbs et al. |
| 5,007,927 A | 4/1991 | Badylak et al. |
| 5,275,826 A | 1/1994 | Badylak et al. |
| 5,281,422 A | 1/1994 | Badylak et al. |
| 5,352,463 A | 10/1994 | Badylak et al. |
| 5,354,274 A | 10/1994 | Demeter et al. |
| 5,372,821 A | 12/1994 | Badylak et al. |
| 5,445,833 A | 8/1995 | Badylak et al. |
| 5,554,389 A | 9/1996 | Badylak et al. |
| 5,573,784 A | 11/1996 | Badylak et al. |
| 5,641,518 A | 6/1997 | Badylak et al. |
| 5,645,860 A | 7/1997 | Knapp, Jr. et al. |
| 5,695,998 A | 12/1997 | Badylak et al. |
| 5,711,969 A | 1/1998 | Patel et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,771,969 A | 6/1998 | Garay |
| 5,866,414 A | 2/1999 | Badylak et al. |
| 5,955,110 A | 9/1999 | Patel et al. |
| 5,968,096 A | 10/1999 | Whitson et al. |
| 6,087,157 A | 6/2000 | Badylak et al. |
| 6,096,347 A | 8/2000 | Geddes et al. |
| 6,099,567 A | 8/2000 | Badylak et al. |
| 6,126,686 A | 10/2000 | Badylak et al. |
| 6,187,039 B1 | 2/2001 | Hiles et al. |
| 6,241,981 B1 | 6/2001 | Cobb et al. |
| 6,331,319 B1 | 12/2001 | Badylak et al. |
| 6,375,989 B1 | 4/2002 | Badylak et al. |

(Continued)

FOREIGN PATENT DOCUMENTS

| | | |
|---|---|---|
| CN | 101636181 A | 1/2010 |
| CN | 101970024 A | 2/2011 |

(Continued)

OTHER PUBLICATIONS

Kantsevoy et al., "Endoscopic mucosal resection and endoscopic submucosal dissection", 2008, Gastrointestinal Endoscopy, vol. 68, No. 1, pp. 11-18. (Year: 2008).*

(Continued)

*Primary Examiner* — Michael B. Pallay
(74) *Attorney, Agent, or Firm* — Klarquist Sparkman, LLP; Susan Alpert Siegel; Gregory K. Scott

(57) ABSTRACT

Methods are disclosed for dissecting a mucosa and a submucosa from a muscularis propria from a region of an organ of a subject, wherein the organ is not the esophagus. In some embodiments, the organ is in the gastrointestinal tract. These methods include injecting submucosally into the organ of the subject a pharmaceutical composition comprising an extracellular matrix (ECM) hydrogel to form a cushion between the submucosa and the underlying muscularis propria at the region of the organ, wherein the ECM hydrogel has the following characteristics: a) a time to 50% gelation of less than 30 minutes at a temperature of about 37° C.; b) a flow viscosity suitable for infusion into the organ; and c) a stiffness of about 10 to about 400 Pascal (Pa).

26 Claims, 9 Drawing Sheets

(56) References Cited

U.S. PATENT DOCUMENTS

| | | |
|---|---|---|
| 6,475,232 B1 | 11/2002 | Babbs et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,918,396 B1 | 7/2005 | Badylak et al. |
| 7,771,717 B2 | 8/2010 | Badylak et al. |
| 7,820,634 B2 | 10/2010 | Badylak et al. |
| 8,003,131 B2 | 8/2011 | Badylak |
| 8,029,774 B2 | 10/2011 | Bekman et al. |
| 8,084,048 B2 | 12/2011 | Badylak |
| 8,361,503 B2 | 1/2013 | Badylak et al. |
| 8,409,625 B2 | 4/2013 | Badylak |
| 8,535,719 B2 | 9/2013 | Badylak et al. |
| 8,647,677 B2 | 2/2014 | Badylak et al. |
| 8,691,276 B2 | 4/2014 | Badylak et al. |
| 8,716,438 B2 | 5/2014 | Agrawal et al. |
| 8,927,003 B2 | 1/2015 | Badylak et al. |
| 9,226,996 B2 | 1/2016 | Moro et al. |
| 9,314,340 B2 | 4/2016 | Badylak et al. |
| 9,364,580 B2 | 6/2016 | Moro et al. |
| 9,421,307 B2 | 8/2016 | Amoroso et al. |
| 9,522,216 B2 | 12/2016 | Moro et al. |
| 9,814,744 B2 | 11/2017 | Badylak et al. |
| 9,861,662 B2 | 1/2018 | Badylak et al. |
| 10,004,827 B2 | 6/2018 | Badylak et al. |
| 10,213,526 B2 | 2/2019 | Badylak et al. |
| 10,286,119 B2 | 5/2019 | Badylak et al. |
| 10,729,813 B2 | 8/2020 | Badylak et al. |
| 10,736,991 B2 | 8/2020 | Badylak et al. |
| 10,933,138 B2 | 3/2021 | Scopton et al. |
| 11,213,545 B2 | 1/2022 | Badylak et al. |
| 11,291,688 B2 | 4/2022 | Badylak et al. |
| 11,389,566 B2 | 7/2022 | Ramer et al. |
| 11,389,569 B2 | 7/2022 | Badylak et al. |
| 11,406,736 B2 | 8/2022 | Badylak et al. |
| 11,638,724 B2 | 5/2023 | Badylak et al. |
| 11,707,485 B2 | 7/2023 | Badylak et al. |
| 2003/0054022 A1 | 3/2003 | Spievack |
| 2003/0065379 A1 | 4/2003 | Babbs et al. |
| 2004/0043006 A1 | 3/2004 | Badylak et al. |
| 2004/0078076 A1 | 4/2004 | Badylak et al. |
| 2004/0176855 A1 | 9/2004 | Badylak |
| 2004/0187877 A1 | 9/2004 | Badylak et al. |
| 2004/0191226 A1 | 9/2004 | Badylak |
| 2005/0025838 A1 | 2/2005 | Badylak |
| 2006/0070631 A1 | 4/2006 | Scopton et al. |
| 2007/0135906 A1 | 6/2007 | Badylak et al. |
| 2008/0260831 A1 | 10/2008 | Badylak et al. |
| 2009/0074732 A1 | 3/2009 | Badylak |
| 2011/0184439 A1 | 7/2011 | Anderson et al. |
| 2011/0208158 A1 | 8/2011 | Sigmon, Jr. et al. |
| 2014/0027149 A1 | 1/2014 | Shimizu et al. |
| 2014/0356331 A1 | 12/2014 | Badylak et al. |
| 2015/0141526 A1 | 5/2015 | Moro et al. |
| 2016/0045552 A1 | 2/2016 | Ramer et al. |
| 2016/0296675 A1 | 10/2016 | Longo et al. |
| 2016/0375177 A1 | 12/2016 | Hauser |
| 2017/0049932 A1 | 2/2017 | Badylak et al. |
| 2018/0155678 A1* | 6/2018 | Francis ................ A61P 1/00 |
| 2018/0200405 A1 | 7/2018 | Badylak et al. |
| 2018/0243473 A1 | 8/2018 | Badylak et al. |
| 2019/0076574 A1 | 3/2019 | Ramer et al. |
| 2019/0117837 A1 | 4/2019 | Badylak et al. |
| 2019/0184060 A1 | 6/2019 | Bulman et al. |
| 2019/0290808 A1 | 9/2019 | Uraoka et al. |
| 2019/0314553 A1 | 10/2019 | Zhang |
| 2020/0030495 A1 | 1/2020 | Badylak et al. |
| 2020/0128711 P1 | 4/2020 | Kordes |
| 2020/0138711 A1 | 5/2020 | De Cola et al. |
| 2020/0261624 A1 | 8/2020 | Crapo et al. |
| 2021/0054027 A1 | 2/2021 | Gianneschi et al. |
| 2021/0268148 A1 | 9/2021 | Badylak et al. |
| 2022/0249549 A1 | 8/2022 | Badylak et al. |
| 2022/0249742 A1 | 8/2022 | Badylak et al. |
| 2022/0331486 A1 | 10/2022 | Badylak et al. |
| 2022/0354473 A1 | 11/2022 | Badylak et al. |

FOREIGN PATENT DOCUMENTS

| | | |
|---|---|---|
| CN | 104689380 A | 6/2015 |
| CN | 104689381 A | 6/2015 |
| CN | 105358094 A | 2/2016 |
| CN | 105920669 A | 9/2016 |
| CN | 106456837 A | 2/2017 |
| CN | 106924809 A | 7/2017 |
| JP | 1996-506799 | 7/1996 |
| JP | 2018-80136 A | 5/2018 |
| WO | WO-1996/024365 | 8/1996 |
| WO | WO-2000/032209 | 6/2000 |
| WO | WO-2003/059221 | 7/2003 |
| WO | WO-2003/059284 | 7/2003 |
| WO | WO-2005/020847 | 3/2005 |
| WO | WO 2008/109407 A2 | 9/2008 |
| WO | WO 2014/168964 A1 | 10/2014 |
| WO | WO 2015/075015 A1 | 5/2015 |
| WO | WO 2015/075024 | 5/2015 |
| WO | WO-2015/143310 | 9/2015 |
| WO | WO 2015/143310 A1 | 9/2015 |
| WO | WO 2017/172588 A1 | 10/2017 |
| WO | WO-2018/005427 | 1/2018 |
| WO | WO 2018/005427 A1 | 1/2018 |
| WO | WO 2018/035491 A1 | 2/2018 |
| WO | WO 2018/161028 A1 | 9/2018 |
| WO | WO-2018/161034 | 9/2018 |
| WO | WO-2018/187286 | 10/2018 |
| WO | WO 2019/246442 | 12/2019 |
| WO | WO 2019/246444 A1 | 12/2019 |
| WO | WO 2019/246447 | 12/2019 |

OTHER PUBLICATIONS

Spang et al., "Extracellular matrix hydrogel therapies: In vivo applications and development", 2018, available online Dec. 20, 2017, Acta Biomaterialia, vol. 68, pp. 1-14. (Year: 2017).*

Badylak et al., "ESOPHAEGL™: Revolutionizing the way we treat esophageal disease," University of Pittsburgh Innovation Institute, Pamphlet, ID: 3936 (2 pages), downloaded on Oct. 19, 2017.

Badylak et al., "Esophageal reconstruction with ECM and muscle tissue in a dog model," *Journal of Surgical Research* 128: 87-97 (2005).

Badylak et al., "Resorbable bioscaffold for esophageal repair in a dog model," *J Pediatr Surg.* 35(7): 1097-1103 (Jul. 2000).

Feitoza et al., "Hydroxypropyl methylcellulose: a better submucosal fluid cushion for endoscopic mucosal resection," *Gastrointestinal Endoscopy* 57(1): 41-47 (2003).

Freytes et al., "Preparation and rheological characterization of a gel form of the porcine urinary bladder matrix," *Biomaterials* 29: 1630-1637 (2008).

Freytes et al., "Preparation and rheological characterization of a gel form of the porcine urinary bladder matrix," *Biomaterials* 29: 1630-1637 (e-Pub Jan. 16, 2008).

Ho and Sly, "Derivation and characterization of murine alternatively activated (M2) macrophages", *Methods Mol Biol.* 531: 173-85 (2009).

International Search Report and Written Opinion from PCT Application No. PCT/US2019/038317, 10 pages (mailed Sep. 18, 2019).

Ishihara et al., "Application of hydrogels as submucosal fluid cushions for endoscopic mucosal resection and submucosal dissection," *J Artif Organs.* 18(3): 191-198 (ePub May 23, 2015) (Abstract only).

(56) References Cited

OTHER PUBLICATIONS

Jung and Park, "Submucosal injection solutions for endoscopic mucosal resection and endoscopic submucosal dissection of gastrointestinal neoplasms," *Gastrointestinal Intervention* 2: 73-77 (2013).
Kakushima and Fujishiro, "Endoscopic submucosal dissection for gastrointestinal neoplasms," *World J Gastroenterol.* 14(19): 2962-2967 (May 21, 2008).
Keane et al., "Tissue-specific effects of esophageal extracellular matrix," *Tissue Engineering: Part A* 21(17-18): 2293-2300 (2015).
Nieponice et al., "An extracellular matrix scaffold for esophageal stricture prevention after circumferential EMR," *Gastrointest Endosc.* 69(2):289-96. doi: 10.1016/j.gie.2008.04.022 (Epub Jul. 26, 2008) (abstract only).
Pati et al., "Printing three-dimensional tissue analogues with decellularized extracellular matrix bioink," *Nature Communication* 4953: 1-11 (Jun. 2, 2014).
Saldin et al., "Extracellular matrix hydrogels from decellularized tissues: Structure and function," *Acta Biomater* 49: 1-5 (e-Pub Dec. 1, 2016).
Scholvinck et al., "Efficacy and safety of a novel submucosal lifting gel used for endoscopic submucosal dissection: a study in a porcine model," *Surg Endosc* 29: 2651-2660 (2015).
Spang et al., "Extracellular matrix hydrogel therapies: in vivo applications and Development," *Acta Biomater* 68: 1-14 (Mar. 1, 2018).
Uraoka et al., "Submucosal injection solution for gastrointestinal tract endoscopic mucosal resection and endoscopic submucosal dissection," *Drug Design, Development and Theory* 2: 131-138 (2008).
Veremeyko et al., "IL-4/IL-13-dependent and independent expression of miR-124 and its contribution to M2 phenotype of monocytic cells in normal conditions and during allergic inflammation," *PLOS ONE* 8(12): e81774, 13 pages, (Dec. 2013).
Wolf et al., "A hydrogel derived from decellularized dermal extracellular matrix," *Biomaterials* 33(29): 7028-7038 (Oct. 2012).
Balmadrid and Hwang, "Endoscopic resection of gastric and esophageal cancer," *Gastroenterology Report* 3(4): 330-338 (Oct. 27, 2015).
Geckil et al., "Engineering hydrogels as extracellular matrix mimics," *Nanomedicine* 5(3): 469-484 (Apr. 16, 2010).
Giannino et al., "Evaluation of Eleview® bioadhesive properties and cushion-forming ability," *Polymers* 12: 346 (Feb. 5, 2020).
Gilbert et al., "A quantitative method for evaluating the degradation of biologic scaffold materials," *Biomaterials* 28: 147-150 (E-pub Sep. 1, 2006).
Hashimoto et al., "The efficacy of endoscopic triamcinolone injection for the prevention of esophageal stricture after endoscopic submucosal dissection," *Gastrointestinal Endoscopy* 74(6): 1389-1393 (Jul. 27, 2011).
Hillegonds et al., "Prime lab sample handling and data analysis for accelerator-based biomedical radiocarbon analysis," *Radiocarbon* 43(2A): 305-311 (E-pub Jul. 18, 2016).
Hussey et al. "Ultrasonic cavitation to prepare ECM hydrogels," *Acta Biomaterialia* 108: 77-86 (E-pub Apr. 5, 2020).
International Search Report and Written Opinion from PCT Application No. PCT/US2019/038315, 9 pages (mailed Aug. 20, 2019).
International Search Report and Written Opinion from PCT Application No. PCT/US2019/038320, 9 pages (mailed Sep. 5, 2019).
Keane et al., "Restoring Mucosal Barrier Function and Modifying Macrophage Phenotype with an Extracellular Matrix Hydrogel: Potential Therapy for Ulcerative Colitis," *Journal of Crohn's and Colitis* 11(3): 360-368 (Sep. 10, 2016).
Kumono et al., "Endoscopic submucosal dissection for pig esophagus by using photocrosslinkable chitosan hydrogel as submucosal fluid cushion," *Gastrointestinal Endoscopy* 75(4): 841-848 (E-pub Jan. 31, 2012).
McGrath et al., "An Extracellular Matrix Scaffold for Esophageal Stricture Prevention After Circumferential EMR," Abstract M1330, *Gastrointestinal Endoscopy* 67(5): AB183 (Apr. 1, 2008).

National Cancer Institute (dysplasia), print-out provided by the U.S. PTO in U.S. Appl. No. 17/688,516, Office action dated Dec. 7, 2022.
Record et al., "In vivo degradation of 14C-labeled small intestinal submucosa (SIS) when used for urinary bladder repair," *Biomaterials* 22(19): 2653-2659 (Oct. 1, 2001).
Database WPI Week 201609, AN 2015-486314, corresponding to Chinese Patent No. CN104689380, *Thomson Scientific, London, GB* (Jun. 10, 2015) (Abstract).
Badylak et al., "Naturally occurring extracellular matrix as a scaffold for musculoskeletal repair," *Clin Orthop* (367 Suppl):S333-343, Oct. 1999.
Badylak et al., "Extracellular matrix as a biological scaffold material: Structure and function," *Acta Biomaterialia* 5(1):1-13, Oct. 2008.
Badylak, "The extracellular matrix as a biologic scaffold material," *Biomaterials* 28 (25):3587-3593, Sep. 2007.
Badylak, "Xenogeneic extracellular matrix as a scaffold for tissue reconstruction," *Transpl Immunol* 12(3-4):367-377, Apr. 2004.
Badylak, "Esophageal tissue engineering," McGowan Institute for Regenerative Medicine, http://www.mirm.pitt.edu/Badylak/projects/Esophageal_Tissue_Engineering.asp, 3 pages (printed to PDF on Dec. 21, 2016).
Badylak et al., "Esophageal preservation in five male patients after endoscopic inner-layer circumferential resection in the setting of superficial cancer: a regenerative medicine approach with a biologic scaffold." *Tissue engineering. Part A* 17(11-12):1643-50, Jun. 2011.
Costa et al., "Biologic Scaffolds," *Cold Spring Harbor perspectives in medicine* 7(9):a025676, Sep. 2017.
Crapo et al., "An Overview of Tissue and Whole Organ Decellularization Processes," *Biomaterials* 32(12):3233-3243, Feb. 2011.
Crapo et al., "Small intestinal submucosa gel as a potential scaffolding material for cardiac tissue engineering," *Acta biomaterialia* 6(6):2091-6, Jun. 2010.
DeMeester et al., "The diagnosis and management of Barrett's esophagus," *Adv Surg* 33:29-68, 1999.
Dequach et al., "Injectable skeletal muscle matrix hydrogel promotes neovascularization and muscle cell infiltration in a hindlimb ischemia model," *Eur Cell Mater* 23:400-12, Jun. 2012.
Doede et al., "Unsuccessful alloplastic esophageal replacement with porcine small intestinal submucosa," *Artificial Organs* 33(4):328-333, Apr. 2009.
Faulk et al., "ECM hydrogel coating mitigates the chronic inflammatory response to polypropylene mesh," *Biomaterials* 35(30);8585-8595, Jul. 2014.
Fercana et al, "Perivascular Extracellular Matrix Hydrogels Mimic Native Matrix Microarchitecture and Promote Angiogenesis via Basic Fibroblast Growth Factor," *Biomaterials* 123:142-154, Jan. 2017.
Freytes et al., "Porcine Urinary Bladder Matrix Derived Gel for Tissue Engineering Applications," *Regenerate World Congress and Society for Biomaterials:* 2006. Pittsburgh, PA. (Poster and Abstract).
Ghuman et al, "Long-term retention of ECM hydrogel after implantation into a sub-acute stroke cavity reduces lesion volume," *Acta Bio mater* 63:50-63, Sep. 2017.
Hong et al., "Mechanical properties and in vivo behavior of a biodegradable synthetic polymer microfiber-extracellular matrix hydrogel biohybrid scaffold," *Biomaterials* 32(13):3387-3394, May 2011.
Huber et al., "Phenotypic changes in cultured smooth muscle cells: limitation or opportunity for tissue engineering of hollow organs?," *Journal of tissue engineering and regenerative medicine* 6(7):505-11, Jul. 2011.
Hussey et al., "Extracellular Matrix Bioscaffolds for Building Gastrointestinal Tissue," *Cellular and molecular gastroenterology and hepatology* 5(1):1-13, Sep. 2017.
Keane et al. "Preparation and characterization of a biologic scaffold from esophageal mucosa," *Biomaterials* 34(28):6729-37, Sep. 2013.
Lehman, "Injectable and bulk-forming agents for enhancing the lower esophageal sphincter," *Am J Med* 18(115 Suppl 3A):188S-191S, Aug. 2003.
Londono et al., "Regenerative Medicine Strategies for Esophageal Repair," *Tissue Eng Part B Rev* 21(4):393-410, Apr. 2015.

(56) References Cited

OTHER PUBLICATIONS

Londono et al., "Esophagus and regenerative medicine," *World J Gastroenterol* 18(47):6894-6899, Dec. 2012.

Massensini et al., "Concentration-dependent rheological properties of ECM hydrogel for intracerebral delivery to a stroke cavity," *Acta Biomateriala.* 27:116-130, Nov. 2015.

Meng et al., "Solubilized extracellular matrix from brain and urinary bladder elicits distinct functional and phenotypic responses in macrophages," *Biomaterials* 46:131-40, Jan. 2015.

Naranjo et al., "Regenerative Medicine: lessons from Mother Nature," *Regenerative medicine* 11(8):767-775, Nov. 2016.

Nieponice et al., "Bone marrow-derived cells participate in the long-term remodeling in a mouse model of esophageal reconstruction," *The Journal of surgical research* 182(1):e1-7, Oct. 2012.

Nieponice et al., "Patch esophagoplasty: esophageal reconstruction using biologic scaffolds," *The Annals of thoracic surgery* 97(1):283-8, Nov. 2013.

Nieponice et al., "Reinforcement of esophageal anastomoses with an extracellular matrix scaffold in a canine model," *The Annals of thoracic surgery* 82(6):2050-8, Dec. 2006.

Repici et al., "A novel submucosal injection solution for endoscopic resection of large colorectal lesions: a randomized, double-blind trial," *Gastrointestinal endoscopy* 88(3):527-535.e5, May 2018.

Ringel et al., "The application of tissue engineering procedures to repair the larynx," *J Speech Lang Hear Res* 49(1):194-208, Feb. 2006.

Saldin et al., "Extracellular Matrix Degradation Products Downregulate Neoplastic Esophageal Cell Phenotype," *Tissue engineering. Part A* 25(5-6):487-498, Mar. 2019.

Santucci et al., "Resorbable extracellular matrix grafts in urologic reconstruction," Int Braz J Urol 31(3):192-203, May-Jun. 2005.

Witteman et al., "Transoral endoscopic inner layer esophagectomy: management of high-grade dysplasia and superficial cancer with organ preservation," *Journal of gastrointestinal surgery : official journal of the Society for Surgery of the Alimentary Tract* 13(12):2104-12, Oct. 2009.

Zhu et al., "Injectable, porous, biohybrid hydrogels incorporating decellularized tissue components for soft tissue applications," *Acta biomaterialia* 73:112-126, Jun. 2018.

\* cited by examiner

Mucoadhesive Strength to Muscle

Mucoadhesive Strength to Mucosa

EXTRACELLULAR MATRIX (ECM) HYDROGEL AS A SUBMUCOSAL FLUID CUSHION

CROSS REFERENCE TO RELATED APPLICATIONS

This is a continuation of U.S. application Ser. No. 17/254,040, filed on Dec. 18, 2020, now abandoned, which is a § 371 U.S. national stage of International Application No. PCT/US2019/038317, filed Jun. 20, 2019, which claims the benefit of U.S. Provisional Application No. 62/688,198, filed Jun. 21, 2018. The prior applications are incorporated by reference herein in their entirety.

FIELD OF THE DISCLOSURE

This relates to endoscopic resection, specifically to the use of an extracellular matrix (ECM) hydrogel as a submucosal cushion for dissecting a mucosa and a submucosa from a muscularis propria from a region of an organ, wherein the organ is not the esophagus.

BACKGROUND

Endoscopy is a procedure that allows examination of the interior of a hollow organ or cavity of the body by means of an instrument called an endoscope, without employing invasive surgery. Endoscopy can be used for surgical procedures such as cauterization of a bleeding vessel, removing polyps, adenomas and small tumors, performing biopsies or removing a foreign object. Endoscopic procedures can be performed in the gastrointestinal tract, the respiratory tract, the ear, the urinary tract, the female reproductive system and, through small incisions, in normally closed body cavities such as the abdominal or pelvic cavity (laparoscopy), the interior of a joint (arthroscopy) and organs of the chest (thoracoscopy and mediastinoscopy). Endoscopy can be performed in the upper gastrointestinal tract or the lower gastrointestinal tract. The endoscope is an illuminated, usually fiber optic, flexible or rigid tubular instrument for visualizing the interior of a hollow organ or part (such as the bladder, esophagus, stomach or intestine) for diagnostic or therapeutic purposes, that typically has one or more working channels to enable passage of instruments (such as forceps, electrosurgical knife, endoscopic injection needles or scissors) or to facilitate the removal of bioptic samples. It includes a suitable lamp and imaging device at its distal portion, and it can be inserted through natural occurring openings of the body, such as the mouth, the anus, the ear, the nose or through small surgical incisions. Given the wide variety of body organs or cavities which can be examined by means of endoscopic procedures, several types of specialized endoscopes exist, such as, for example, laryngoscope, thoracoscope, angioscope, colonoscope, enteroscope, sigmoidoscope, rectoscope, proctoscope, anoscope, arthroscope, rhinoscope, laparoscope, hysteroscope, encephaloscope, nephroscope, esophagoscope, bronchoscope, gastroscope, amnioscope, cystoscope.

Endoscopic procedures are widely applied in the gastrointestinal tract, including the upper and the lower gastrointestinal tract. For example, endoscopic procedures can be used to examine the mucosa that covers the gastrointestinal cavities, and to detect small and large pathological lesions, such as inflammatory tissue, polyps, pseudo-polyps, serrated lesions, adenomas, ulcerations, dysplasias, pre-neoplastic and neoplastic formations, and tumors. Endoscopic procedures can be used for biopsies and removal of pathologic lesions (polyps, adenomas, dysplasias, pre-neoplastic and neoplastic formations, tumors). Surgical interventions include two types of endoscopic resection procedures commonly used in gastrointestinal endoscopy to remove pathological lesions: endoscopic mucosal resection (EMR) and endoscopic submucosal dissection (ESD). These two techniques allow for minimally invasive treatment of gastrointestinal polyps, adenomas, dysplasias, and early-stage cancers that involve a minimum risk of lymph-node metastasis. A need remains for agents of use in these procedures.

SUMMARY OF THE DISCLOSURE

Methods are disclosed herein for dissecting a mucosa and a submucosa from a muscularis propria from a region of an organ of a subject, wherein the organ is not the esophagus. These methods include injecting submucosally into the organ of the subject a pharmaceutical composition comprising an extracellular matrix (ECM) hydrogel to form a cushion between the submucosa and the underlying muscularis propria at the region of the organ, wherein the ECM hydrogel has the following characteristics:

a) a time to 50% gelation of less than 30 minutes at a temperature of about 37° C.;
b) a flow viscosity suitable for infusion into the organ; and
c) a stiffness of about 10 to about 400 Pascal (Pa);
thereby dissecting the mucosa and the submucosa from the underlying muscularis propria and inhibiting inflammation in the region of the organ.

In other embodiments, these methods include injecting submucosally into the organ of the subject a pharmaceutical composition comprising an extracellular matrix (ECM) hydrogel to form a cushion between the submucosa and the underlying muscularis propria in the region of the organ, thereby dissecting the mucosa and the submucosa from the underlying muscularis propria and inhibiting inflammation in the region of the organ.

The organ can be an organ of the gastrointestinal tract, including the upper or lower gastrointestinal tract. Exemplary organs include, but are not limited to, the stomach, small intestine, large intestine (colon including the transverse, ascending, or descending colon), or rectum.

In some embodiments, the method of dissecting comprises endoscopic mucosal resection or endoscopic mucosal dissection.

The foregoing and other features and advantages of the invention will become more apparent from the following detailed description of several embodiments which proceeds with reference to the accompanying figures.

DETAILED DESCRIPTION OF SEVERAL EMBODIMENTS

Figure 1A:
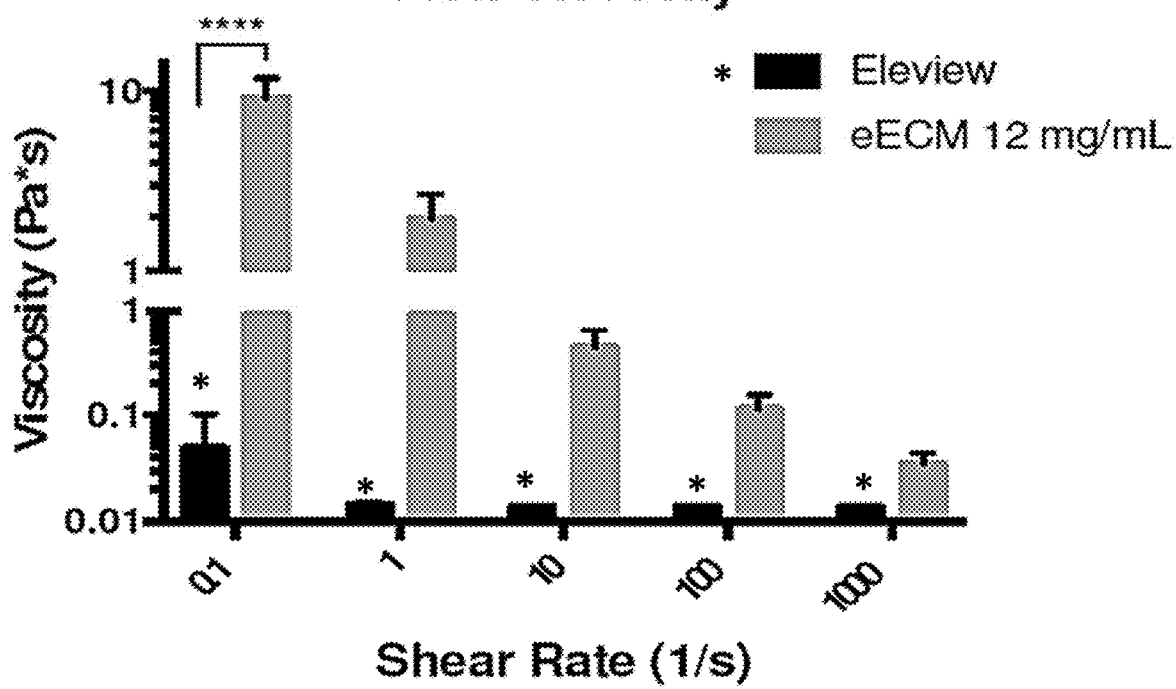
FIGS. 1A-1E. Viscoelastic properties. The viscosity profile of ELEVIEW™ and esophageal (eECM) 12 mg/mL was tested with increasing shear rate (0.1-1000 1/s) at 10° C. (A). Temperature was rapidly raised to 37° C. to induce gelation and to measure the maximum storage (G') and loss modulus (G") (B). Representative graphs of the time sweep are shown for ELEVIEW™ (C) and eECM hydrogel at 12 mg/mL (D). Time to 50% gelation was measured for eECM 12 mg/mL but could not be measured for ELEVIEW™, because ELEVIEW™ did not gel (G">G' during the timesweep test) (E).

Methods are disclosed herein for dissecting a mucosa and a submucosa from a muscularis propria from a region of an organ of a subject, wherein the organ is not the esophagus. In some embodiments, the organ is in the gastrointestinal tract. These methods include injecting submucosally into the organ of the subject a pharmaceutical composition comprising an extracellular matrix (ECM) hydrogel to form a cushion between the submucosa and the underlying muscularis propria at the region of the organ. The organ can be, for example, the stomach, small intestine, large intestine (colon including the transverse, ascending, or descending colon) or rectum.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Acid Protease: An enzyme that cleaves peptide bonds, wherein the enzyme has increased activity of cleaving peptide bonds in an acidic pH. For example and without limitation, acid proteases can include pepsin and trypsin.

Base: A compound or a solution of a compound with a pH greater than 7. For example and without limitation, the base is an alkaline hydroxide or an aqueous solution of an alkaline hydroxide. In certain embodiments, the base is NaOH or NaOH in PBS.

Comminute (comminution and comminuting): The process of reducing larger particles into smaller particles, including, without limitation, by grinding, blending, shredding, slicing, milling, cutting, or shredding. ECM can be comminuted while in any form, including, but not limited to, hydrated forms, frozen, air-dried, lyophilized, powdered, sheet-form.

Colon Cancer: A cancer of the large intestine. Tubular adenoma is a type of colonic polyp and a precursor of colorectal cancer. Colon cancer can be, for example, a colonic carcinoid or an adenocarcinoma. Colorectal cancer diagnosis is performed by sampling of areas of the colon suspicious for possible tumor development, typically during colonoscopy or sigmoidoscopy, depending on the location of the lesion.

Diagnosis: The process of identifying a disease by its signs, symptoms and results of various tests. The conclusion reached through that process is also called "a diagnosis." Forms of testing commonly performed include blood tests, medical imaging, and biopsy.

Dissection: The process of separating or cutting apart tissues, for example, during a surgical procedure.

Endoscopic injection needles or endoscopic injection needle catheters: Devices which are generally long (for example, up to about 230 cm) and which include a long catheter within which an inner injection tube having a distal injection needle that is slideably disposed. Generally, a proximal actuating handle is coupled to the catheter and the injection tube for moving one relative to the other. The needle can be retractable. Fluid access to the injection tube is typically provided via a luer connector on the handle.

Endoscopic injection needles are typically delivered to the injection site through the catheter of the endoscope. To protect the lumen from damage, the handle of the infusion needle device is manipulated to withdraw the distal injection needle into the lumen of the catheter before inserting the device into the endoscope. When the distal end of the endoscopic injection needle device is located at the injection site, its handle is manipulated to move the injection needle distally out of the lumen of the catheter. In some embodiments, when advanced to the most distal position, the exposed portion of the injection needle can be about 4-6 mm in length.

Endoscopic Mucosal resection (EMR): An endoscopic technique developed for removal of sessile or flat neoplasms confined to the superficial layers (mucosa and submucosa) of the gastrointestinal (GI) tract. The mucosa and submucosa are resected from the underlying muscularis propria. An endoscopic mucosal dissection (ESD) refers to an endoscopic technique developed specifically for removing larger lesions, such as from the gastrointestinal tract, wherein the mucosa and submucosa are dissected from the other layers of the gastrointestinal tract. Both EMR and EMD typically involve injection of a substance under the targeted lesion, between the submucosa and underlying muscularis propria, to act as a cushion and elevate the submucosa and overlying mucosa. With EMR, the elevated lesion is then removed with a snare, mobilized into a small cup by suction. With ESD, the submucosa under the lesion is dissected with a specialized knife, causing separation of the submucosa and overlying mucosa. ESD enables removal of larger and potentially deeper lesions than possible with EMR with a curative intent. Both EMR and ESD are facilitated by injection of a substance into the submucosal plane of the organ, which effectively separates the overlying mucosa from the underlying muscularis propria, and simultaneously elevates the mucosa above the adjacent esophageal mucosa. This separation of layers and elevation of affected tissue helps the surgeon isolate, grasp, and remove the tissue of interest.

Extracellular Matrix (ECM): The non-cellular component of tissues and organs. Natural ECM (ECM found in multicellular organisms, such as mammals and humans) is a complex mixture of structural and non-structural biomolecules, including, but not limited to, collagens, elastins, laminins, glycosaminoglycans, proteoglycans, antimicrobials, chemoattractants, cytokines, and growth factors, and typically differs in the specific composition between different tissues and organs. In mammals, ECM often comprises about 90% collagen by dry weight mass, in its various forms. Biologic scaffolds composed of ECM can be created by removing the cells from a given tissue or organ leaving behind the ECM. The composition and structure of ECM varies depending on the anatomic source of the tissue. For example, small intestinal submucosa (SIS), urinary bladder matrix (UBM), esophagus (E) and liver stroma ECM each differ in their overall structure and composition due to the unique cellular niche needed for each tissue. An intact "extracellular matrix" and "intact ECM" bioscaffold consists of extracellular matrix that has not been solubilized, retains its' 3-dimensional ultrastructure, and ideally retains activity of its structural and non-structural biomolecules, including, but not limited to, collagens, elastins, laminins, glycosaminoglycans, proteoglycans, antimicrobials, chemoattractants, cytokines, and growth factors, such as, without limitation comminuted ECM as described herein.

The activity of the biomolecules within the ECM can be altered chemically or mechanically, for example, by chemical or enzymatic cross-linking and/or by dialyzing the ECM. Intact ECM essentially has not been enzymatically digested, cross-linked and/or dialyzed, meaning that the ECM has not been subjected to a digestion, dialysis and/or a cross-linking process, or conditions other than processes that occur naturally during storage and handling of ECM prior to solubilization. Thus. ECM that is dialyzed (in anything but a trivial manner which does not substantially affect the gelation and functional characteristics of the ECM in its uses described herein) is not considered to be "intact."

Esophagogastroduodenoscopy (EGD) or Upper Gastrointestinal Endoscopy: A diagnostic endoscopic procedure that visualizes any upper part of the gastrointestinal tract up to the duodenum. An endoscopy may sometimes be performed as part of an EGD or upper gastrointestinal endoscopy. The terms are not mutually exclusive unless expressly stated to be so.

Gastrointestinal tract: The organ system in mammals which takes in food, digest it, and expel the remaining waste. The buccal cavity, pharynx, esophagus, stomach, and duodenum form the upper gastrointestinal tract. The lower gastrointestinal tract includes the small intestine, large intestine (colon), and rectum.

Gelation: The formation of a gel from a sol.

Flow Viscosity: A measure of the resistance of a fluid to gradual deformation by shear stress or tensile stress. Viscosity is a property of a fluid which opposes the relative motion between the two surfaces of the fluid in a fluid that are moving at different velocities. When a fluid is forced through a tube, particles that compose the fluid generally move more quickly near the tube's axis and more slowly near its walls. Stress (such as a pressure difference between the two ends of the tube) is needed to overcome the friction between particle layers to keep the fluid moving. For a given velocity pattern, the stress required is proportional to the fluid's viscosity. Viscosity is measured with viscometers and rheometers. Viscosity can be measured as pascal second (Pa*s). Water at 20° C. has a viscosity of 1.002 mPa*s.

Hydrogel: A network of polymer chains that are hydrophilic, sometimes found as a colloidal gel in which water is the dispersion medium. Hydrogels are highly absorbent natural or synthetic polymeric networks. Hydrogels also possess a degree of flexibility similar to natural tissue. The term "urinary bladder ECM hydrogel" includes UBM and UBS hydrogels.

Inflammation: A localized response elicited by injury to tissue. Inflammation is characterized by the appearance in or migration into any tissue space, unit or region of any class of leukocyte in numbers that exceed the number of such cells found within such region of tissue under normal (healthy) circumstances. Inflammation is orchestrated by a complex biological response of vascular tissues to harmful stimuli, such as pathogens, damaged cells, or irritants.

Isotonic Buffered Solution: A solution that is buffered to a pH between 7.2 and 7.8 and that has a balanced concentration of salts to promote an isotonic environment.

Low Grade Dysplasia and High Grade Dysplasia and Metaplasia: Pathological conditions are characterized by an abnormal cell morphology, but the cell type is still recognizable as squamous epithelium. Generally, in dysplasia there is an absence of apical mucin in the internal lining cells of the portion of the gastrointestinal tract. At low power, these areas may appear more hyperchromatic as compared to uninvolved areas.

For high grade dysplasia, the changes in cell morphology become more pronounced, but the cells are still technically a type of squamous epithelium.

When the cells change from squamous epithelial cells to another cell type, such as a glandular cell that often is cuboidal or columnar in shape, the process is referred to as metaplasia. With metaplasia, the distortion of glandular architecture of the tissue is usually present and may be marked; it is composed of branching and lateral budding of crypts, a villiform configuration of the mucosal surface, or intraglandular bridging of epithelium to form a cribriform pattern of "back-to-back" glands. There is abnormal epithelium on the mucosal surface with loss of nuclear polarity, characterized by "rounding up" of the nuclei, and absence of a consistent relationship of nuclei to each other.

Preventing or treating: Inhibiting a disease refers to inhibiting the partial or full development of a disease, for example in a person who is at risk for a disease such as one caused by inflammation. Inhibiting a disease process includes preventing the development of the disease. "Treatment" refers to a therapeutic intervention that ameliorates a sign or symptom of a disease or pathological condition, such as after it has begun to develop.

Sheer Stress: The component of stress coplanar with a material cross section. Shear stress arises from the force vector component parallel to the cross section. The formula to calculate average shear stress is force per unit area $$\tau = \frac{F}{A},$$

where $\tau$=the shear stress, F=the force applied, A=the cross-sectional area of material with area parallel to the applied force vector.

Stiffness: The rigidity of an object or fluid. The stiffness of the extracellular matrix is important for guiding the migration of cells in durotaxis. Stiffness can be measure in Pascal (Pa), which are one newton per square meter.

Therapeutic agent: Used in a generic sense, it includes treating agents, prophylactic agents, and replacement agents. "Treatment" or "treating" means providing a substance, such as a ECM hydrogel, to a patient in an amount sufficient to measurably reduce, inhibit, or mitigate any disease symptom, slow disease progression, or cause disease regression. In certain embodiments treatment of the disease may be commenced before the patient presents symptoms of the disease. The disclosed methods inhibit esophageal inflammation and/or mitigate the effects of esophageal inflammation.

Therapeutically effective amount: A "therapeutically effective amount" of a composition, such as an ECM hydrogel, means an amount effective, when administered to a patient, to provide a therapeutic benefit such as an amelioration of symptoms, reduced decrease progression, or cause disease regression. A quantity of an ECM hydrogel is therapeutically effective if it is sufficient to achieve a desired effect in a subject being treated, such as to form a gel when injected into the submucosal tissue of an organ and dissect the overlying mucosa from the underlying muscularis propria.

The effective amount to form a submucosal cushion will be dependent on the preparation applied, the subject being treated, the severity and type of the affliction, and the manner of administration. The ECM hydrogels of use in the methods disclosed herein have applications in both medical and veterinary settings. Therefore, the general term "subject" or "patient" is understood to include all animals, including, but not limited to, humans or veterinary subjects, such as other primates, dogs, cats, horses, and cows.

Urinary Bladder ECM: An extracellular matrix derived from urinary bladder of any mammal. This term includes urinary bladder matrix (UBM) ECM, and urinary bladder submucosa (UBS) ECM. The wall of the urinary bladder is composed of the following layers: the tunica mucosa (including a transitional epithelium layer and the tunica propria), a submucosa layer, up to three layers of muscle and the adventitia (a loose connective tissue layer)—listed in thickness cross-section from luminal to abluminal sides. UBS is prepared from a tissue composition comprising bladder submucosal tissue delaminated from abluminal muscle layers and at least the luminal portion of the tunica mucosa of a segment of vertebrate urinary bladder, see U.S. Pat. No. 5,554,389, incorporated herein by reference). UBM ECM is prepared from urinary bladder epithelial basement membrane and the tunica propria that is immediately subjacent to the basement membrane, see U.S. Pat. No. 6,576,265, incorporated herein by reference.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The term "about" indicates within 5 percent. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Extracellular Matrix (ECM) Hydrogels

Methods of preparing ECM hydrogels, are disclosed for example, in U.S. Pat. No. 8,361,503. Any type of extracellular matrix tissue can be used to produce a hydrogel which can be used in the methods as disclosed herein (see U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666 related to ECM). In certain embodiments, the ECM is isolated from a vertebrate animal, for example and without limitation, from a warm-blooded mammalian vertebrate animal including, but not limited to, humans, monkeys, horses, pigs, cows and sheep. In specific non-limiting examples, the ECM is porcine or human.

The ECM can be derived from any organ or tissue, including without limitation, urinary bladder, intestine, large intestine (colon), liver, esophagus and dermis. The ECM may be derived from kidney, heart, uterus, brain, blood vessel, lung, bone, muscle, pancreas, stomach, spleen, or colon. In one embodiment, the ECM is isolated from a urinary bladder. In another embodiment, the ECM is from an esophagus. The ECM may or may not include the basement membrane portion of the ECM. In certain embodiments, the ECM includes at least a portion of the basement membrane. In other embodiments, the ECM is harvested from a cell culture. The ECM hydrogel can be produced by a combination of two or more tissue sources.

As disclosed in U.S. Pat. No. 8,361,503 (incorporated herein by reference), a urinary bladder ECM, such as porcine bladder ECM is prepared by abrading bladder tissue to remove the outer (abluminal) layers including both the tunica serosa, the tunica muscularis externa, the tunica submucosa using a longitudinal wiping motion with a scalpel handle and moistened gauze.

Following eversion of the tissue segment, the luminal portion of the tunica mucosa is delaminated form the underlying tissue using the same wiping motion. The tunica serosa, tunica muscularis externa, tunica submucosa and most of the muscularis mucosa can be removed by a combination of enzymatic treatment, hydration, and abrasion. In some embodiments, mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. In other embodiments, the epithelial cells of the tunica mucosa can also be dissociated by soaking the tissue in a de-epithelializing solution, for example and without limitation, hypertonic saline. The resulting UBM comprises basement membrane of the tunica mucosa and the adjacent tunica propria, which is further treated with peracetic acid, lyophilized and powdered, see U.S. Pat. No. 8,361,503.

In another embodiment, the ECM is derived from urinary bladder. Methods for producing a urinary bladder matrix (UBM) ECM are disclosed in U.S. Pat. No. 6,576,265, incorporated herein by reference. Methods for producing a urinary bladder submucosa (UBS) ECM are disclosed in U.S. Pat. No. 5,554,389, incorporated herein by reference. These types of urinary bladder ECM are both of use in the methods disclosed herein. Commercially available preparations off UBM can be utilized (Acell Corporation; Jessup, Md.).

U.S. Pat. No. 6,893,666, incorporated herein by reference, also discloses production of ECM from urinary bladder, skin, esophagus and small intestine. The production of hydrogels from decellularized dermal ECM is disclosed in Wolf et al., Biomaterials 33: 7028-7038, 2012, incorporated herein by reference. The production of ECM from esophageal tissue is disclosed, for example, in Badylak et al. J Pediatr Surg. 35(7):1097-103, 2000 and Badylak et al., J. Surg. Res. 2005 September; 128(1):87-97, 2005, both incorporated herein by reference.

Commercially available ECM preparations can also be used in the methods, devices and compositions described herein. In one embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and CRAFTPATCH™ (Organogenesis Inc.; Canton Mass.). In another embodiment, the ECM is derived from dermis. Commercially available preparations include, but are not limited to IPELVICOL™ (sold as PERMACOL™ in Europe; Bard, Covington, Ga.), REPLIFORM™ (Microvasive; Boston, Mass.) and ALLODERM™ (LifeCell; Branchburg, N.J.). A commercially available UBM ECM is MATRISTEM UBM™ (Acell, Layfayette, IN).

Source tissue used for preparation of ECM can be harvested in a large variety of ways and once harvested, a variety of portions of the harvested tissue may be used. ECM has also been prepared from the esophagus and small intestine, and hydrogels have been prepared from this ECM, see, for example, Keane et al., Tissue Eng. Part A, 21(17-18): 2293-2300, 2015, incorporated herein by reference. Esophageal ECM can be prepared by mechanically separating the mucosa and submucosa from the muscularis externa and digesting the mucosal layers in a buffer including trypsin, followed by exposure to sucrose, TRITON-X100®, deoxycholic acid, peracetic acid and DNAse. Small intestinal submucosa (SIS) can be prepared by mechanically removing the superficial layers of the tunica mucosa, tunica serosa, and tunica muscularis externa from the intact small intestine, leaving the submucosa, muscularis mucosa, and basilar stratum compactum intact. The SIS is then treated with peracetic acid. Exemplary protocols are provided in Keane et al.

In some embodiments, the epithelial cells can be delaminated by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

ECM can be disinfected or sterilized by any number of standard techniques, including, but not limited to, exposure to peracetic acid, low dose gamma radiation, gas plasma sterilization, ethylene oxide treatment, supercritical $CO_2$, or electron beam treatment. More typically, disinfection of ECM is obtained by soaking in 0.1% (v/v) peracetic acid, 4% (v/v) ethanol, and 95.9% (v/v) sterile water for two hours. The peracetic acid residue is removed by washing twice for 15 minutes with PBS (pH=7.4) and twice for 15 minutes with sterile water. ECM material can be sterilized by propylene oxide or ethylene oxide treatment, gamma irradiation treatment (0.05 to 4 mRad), gas plasma sterilization, supercritical $CO_2$, or electron beam treatment. The ECM can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. As disclosed in U.S. Pat. No. 8,361,503. ECM is disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water.

Following isolation of the tissue of interest, decellularization is performed by various methods, for example and without limitation, exposure to hypertonic saline, peracetic acid, TRITON-X® or other detergents. Disinfection and decellularization can be simultaneous. For example, and without limitation, disinfection with peracetic acid, described above, also can serve to decellularize the ECM. Decellularized ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state.

In order to prepare solubilized ECM tissue for use in preparing an ECM hydrogel, comminuted ECM is digested with an acid protease in an acidic solution to form a digest solution. The digest solution of ECM typically is kept at a constant stir for a certain amount of time at room temperature. The ECM digest can be used immediately or be stored at −20° C. or frozen at, for example and without limitation, −20° C. or −80° C.

Once the ECM is solubilized (typically substantially completely) the pH of the solution is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. This forms a "pre-gel" solution. The pre-gel is in liquid form as a viscous solution at room temperature. The neutralized digest solution (pre-gel) can be gelled at temperatures approaching 37° C., wherein the temperature approaches physiological temperature. The method typically does not include a dialysis step prior to gelation, yielding a more-complete ECM-like matrix that typically gels at 37° C. at specific rates (see below).

Thus, the ECM typically can be derived from mammalian tissue, such as, without limitation from one of urinary bladder, dermis, esophagus, small intestine, kidney, liver, heart, uterus, brain, blood vessel, lung, bone, muscle, pancreas, stomach, spleen, or colon. The ECM hydrogel can be produced from two or more tissue sources, such as 2, 3, or 4 tissue sources. In one non-limiting embodiment, the ECM is lyophilized and comminuted. The ECM is then solubilized with an acid protease in an acidic solution to produce digested ECM, such as esophageal ECM. The acid protease may be, without limitation, pepsin or trypsin, or a combination thereof. The ECM can then be solubilized at an acid pH suitable or optimal for the protease, such as greater than about pH or between pH and 4, for example in a 0.01M HCl solution. The solution typically is solubilized for about 12 to about 48 hours, depending upon the tissue type (e.g., see examples below), with mixing (stirring, agitation, admixing, blending, rotating, tilting, etc.). ECM hydrogel is prepared by (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution (pre-gel solution), and (iv) gelling the solution at a temperature of approximately 37° C. within the organ of a subject of interest. When an acid protease is used to digest the ECM, the pre-gel solution and the resulting hydrogel may contain inactivated protease.

The ECM hydrogel, when exposed to temperatures of about 37° C., forms the gel. The ECM hydrogel in the "pre-gel" form can be frozen and stored at, for example and without limitation, −20° C. or −80° C. The ECM hydrogel in the "pre-gel" form can be stored at room temperature, such about 25° C. Thus, the ECM hydrogel is in the pre-gel form at below 37° C., such as at 25, 24, 23, 22, 21, 20, 19, 18, 17, 16, 15, 14, 13, 12, 11, 10, 9, 8, 7, 6, 5, 4° C. The ECM hydrogel can be frozen for storage, and thus, can be stored at below 0° C. As used herein, the term "pre-gel form" or "pre-gel" refers to the ECM hydrogel wherein the pH is increased, but has not gelled. For example, and without limitation, an ECM hydrogel in the pre-gel form has a pH between 7.2 and 7.8. The ECM hydrogel can be delivered in a pre-gel form to a subject using an endoscope.

The ECM hydrogel in the pre-gel form is amenable to introduction into the organ of a patient, such as an organ of the gastrointestinal tract that is not the esophagus. Once introduced submucosally into the organ, which is approximately 37° C., the ECM hydrogel gels and creates a cushion of ECM hydrogel between the muscularis propria and the submucosa of the organ, lifting the submucosa for surgical resection. Without being bound by theory, the ECM hydrogel includes many native soluble factors, such as, but not limited to, cytokines. The specific characteristics of non-dialyzed (whole ECM) preparations prepared from a variety of tissues are disclosed herein.

In some embodiments, the ECM hydrogel has the following characteristics: a) a time to 50% gelation of less than 30 minutes at a temperature of about 37° C.; b) a flow viscosity suitable for infusion into the organ; and c) a stiffness of i) about 10 to about 400 Pascal (Pa), ii) about 10 to about 450 Pa; iii) about 10 to about 600 Pa, iv) about 5 to about 1,000 Pa, v) about 10 to 1,000 Pa, or vi) about 10 to about 70 Pa.

In embodiments, the ECM hydrogel has the following characteristics: a) a time to 50% gelation of less than 30 minutes at a temperature of about 37° C.; b) a flow viscosity suitable for infusion into the organ; and c) a stiffness of about 10 to about 300 Pascal (Pa). In other embodiments, the ECM hydrogel has the following characteristics: a) a time to 50% gelation of less than 30 minutes at a temperature of about 37° C.; b) a flow viscosity suitable for infusion into the organ; and c) a stiffness of about 10 to about 450 Pascal (Pa). In other embodiments, the ECM hydrogel has the following characteristics: a) a time to 50% gelation of less than 30 minutes at a temperature of about 37° C.; b) a flow viscosity suitable for infusion into the organ; and c) a stiffness of about 10 to about 600 Pascal (Pa).

In other embodiments, the ECM hydrogel has the following characteristics: a) a time to 50% gelation of less than 30 minutes at a temperature of about 37° C.; b) a flow viscosity suitable for infusion into the organ; and c) a stiffness of about 5 to about 1,000 Pascal (Pa). In other embodiments, the ECM hydrogel has the following characteristics: a) a time to 50% gelation of less than 30 minutes at a temperature of about 37° C.; b) a flow viscosity suitable for infusion into the organ; and c) a stiffness of about 10 to about 1,000 Pascal (Pa). In more embodiments, the ECM hydrogel has the following characteristics: a) a time to 50% gelation of less than 30 minutes at a temperature of about 37° C.; b) a flow viscosity suitable for infusion into the organ; and c) a stiffness of 10-70 Pascal (Pa). The organ can be any organ of the gastrointestinal tract, with the exception of the esophagus.

In some embodiments, the ECM hydrogel has the following characteristics: a) a time to 50% gelation of less than 30 minutes at a temperature of about 37° C.; b) a flow viscosity suitable for infusion into the organ; and c) a stiffness of i) about 10 to about 400 Pascal (Pa), ii) about 10 to about 450 Pa; iii) about 10 to about 600 Pa, iv) about 5 to about 1,000 Pa, v) about 10 to 1,000 Pa, or vi) about 10 to about 70 Pa.

In some embodiments, the ECM hydrogel has the following characteristics: a) a time to 50% gelation of less than 20 minutes at a temperature of about 37° C.; b) a flow viscosity suitable for infusion into the organ; and c) a stiffness of i) about 10 to about 400 Pascal (Pa), ii) about 10 to about 450 Pa; iii) about 10 to about 600 Pa, iv) about 5 to about 1,000 Pa, v) about 10 to 1,000 Pa, or vi) about 10 to about 70 Pa.

In embodiments, the ECM hydrogel has the following characteristics: a) a time to 50% gelation of less than 20 minutes at a temperature of about 37° C.; b) a flow viscosity suitable for infusion into the organ; and c) a stiffness of about 10 to about 300 Pascal (Pa). In other embodiments, the ECM hydrogel has the following characteristics: a) a time to 50% gelation of less than 20 minutes at a temperature of about 37° C.; b) a flow viscosity suitable for infusion into the organ; and c) a stiffness of about 10 to about 450 Pascal (Pa). In other embodiments, the ECM hydrogel has the following characteristics: a) a time to 50% gelation of less than 20 minutes at a temperature of about 37° C.; b) a flow viscosity suitable for infusion into the organ; and c) a stiffness of about 10 to about 600 Pascal (Pa).

In other embodiments, the ECM hydrogel has the following characteristics: a) a time to 50% gelation of less than 20 minutes at a temperature of about 37° C.; b) a flow viscosity suitable for infusion into the organ; and c) a stiffness of about 5 to about 1,000 Pascal (Pa). In other embodiments, the ECM hydrogel has the following characteristics: a) a time to 50% gelation of less than 20 minutes at a temperature of about 37° C.; b) a flow viscosity suitable for infusion into the organ; and c) a stiffness of about 10 to about 1,000 Pascal (Pa). In more embodiments, the ECM hydrogel has the following characteristics: a) a time to 50% gelation of less than 20 minutes at a temperature of about 37° C.; b) a flow viscosity suitable for infusion into the organ; and c) a stiffness of 10-70 Pascal (Pa).

In another embodiment, the ECM hydrogel has the following characteristics a) a time to 50% gelation of less than ten minutes at about 37° C.; b) a flow viscosity sufficient for injection into the organ; c) a stiffness of about 10 to about 300 Pascal (Pa); and d) the hydrogel is an esophageal hydrogel.

In specific non-limiting examples, the ECM hydrogel is an esophageal hydrogel. In other specific non-limiting examples, the ECM hydrogel can be produced from two or more tissue sources. In further non-limiting examples, the ECM hydrogel can be produced from urinary bladder or small intestine. The ECM hydrogel can be a UBM ECM or a UBS ECM.

In additional specific non-limiting examples, the ECM hydrogel is produced by (a) solubilizing acellular extracellular matrix (ECM) by digestion of tissue with an acid protease in an acidic solution to produce digested esophageal ECM; (b) raising the pH of the digested ECM to a pH between 7.2 and 7.8 to produce a neutralized digest solution; (c) diluting the digested ECM to a concentration of about 2 mg/ml to about 16 mg/ml, such as about 8 mg/ml to about 12 mg/ml of the ECM hydrogel. This hydrogel is then introduced into the organ of the subject, wherein it gels. The ECM can be esophageal ECM.

The ECM hydrogels of use in the methods disclosed herein have a time to 50% gelation of less than 30 minutes at a temperature of about 37° C., such as less than 29, 28, 27, 26, 25, 24, 23, 22, 21, 20, 19, 18, 17, 16, 15, 14, 13, 12, 1, 10, 9, 8, 7, 6, 5, 4, 3 minutes. In some embodiments, the ECM hydrogels have a time to 50% gelation of less than 10 minutes at a temperature of about 37° C. In some embodiments, the time to 50% gelation is about 2 to about 30 minutes at about 37° C. In additional embodiments, the time to 50% gelation is about 2 to about 10 minutes at about 37° C. In more embodiments, the time to 50% gelation is about 3 to about 10 minutes. In other embodiments, the time to 50% gelation is about 3 to about 30 minutes at a temperature of about 37° C. In further embodiments, the time to 50% gelation is about 4 to about 10 minutes at a temperature of about 37° C. In yet other embodiments the time to 50% gelation is about 5 to about 10 minutes or about 10 to about 20 minutes at a temperature of about 37° C.

The disclosed ECM hydrogels can have a flow viscosity suitable for infusion into the organ. In some embodiments, the ECM hydrogel has a flow viscosity of about 10 to about 100 Pa*s at a shear rate of 0.2/s, such as about 10, 20, 30, 40, 50, 60, 70, 80, or 90 Pa*s at a sheer rate of 0.2/s. In further embodiments, the flow viscosity is about 0.1 to about 100 Pa*s at a shear rate of about 0.1/s and is about 0.01 to about 0.2 Pa*s at a shear rate of 1000/s. In more embodiments, the flow viscosity is about 0.1 to about 30 Pa*s at a shear rate of 1/s, and is about 0.02 to about 0.8 Pa*s at a shear rate of about 100/s.

In some embodiments, the ECM hydrogel has a flow viscosity is about 0.1 to about 30 Pa*s at a shear rate of 1/s. In further embodiments, the ECM hydrogel has flow viscosity is about 0.1 to about 100 Pa*s at a shear rate of about 0.1/s. In specific non-limiting examples, the ECM hydrogel has a flow viscosity of 0.5 to about 50 Pa*s, or the ECM hydrogel has a flow viscosity of about 1 to about 40 Pa*s at a shear rate of 0.1/s. Exemplary flow viscosities are about 0.1, 0.5, 1, 2, 3, 4, 5, 6, 7, 8, 9, 10, 15, 20, 25, 30, 35, 40, 50, 60, 70, 80 90 or 100 Pa*s at a shear rate of 0.1/s.

In other embodiments, the ECM hydrogel has a flow viscosity of about 0.01 to about 0.20 Pa*s at a shear rate of 1000/s, or of about 0.01 to about 0.10 Pa*s at a shear rate of 1000/s, such as about 0.01, 0.02, 0.03, 0.04, 0.05, 0.06, 0.07, 0.08, 0.09, 0.10, 0.11, 0.12, 0.13, 0.14, 0.15, 0.16, 0.17, 0.19 or 0.2 at a shear rate of 1000/s.

In more embodiment, the ECM hydrogel has about 0.02 to about 0.8 Pa*s at a shear rate of 100/s, or of about 0.1 to about 0.8 Pa*s at a shear rate of 100/s, such as about 0.02, 0.03, 0.04, 0.05, 0.06, 0.07, 0.08, 0.09, 0.1, 0.2, 0.3, 0.4, 0.5, 0.6, 0.7, or 0.08 Pa*s.

In other embodiments, the ECM hydrogel has a flow viscosity of about 0.1 to about 30 Pa*s, such as about 1 to about 20 Pa*s, or 1 to about 10 Pa*s, or 0.5 to 25 Pa*s, at a shear rate of 1/s, such as about 0.1, 0.2, 0.3, 0.4, 0.5, 0.6, 0.7, 0.8, 0.9, 1, 2, 3, 4, 5, 6, 7, 8, 9, 10, 15, 20, 25 or 30 Pa*s at a shear rate of 1/s. The shear rate can be, for example, 5, 10, 20, or 30 Pa*s at a shear rate of 1/s. In other embodiments, the ECM hydrogel has a flow viscosity of about 0.02 to about 0.8 at a shear rate of 100/s, such as about 0.02, 0.03, 0.04, 0.05, 0.06, 0.07, 0.08. 0.1, 0.2, 0.3, 0.4, 0.5, 0.6, 0.7, or 0.8 at a shear rate of 100/s. The flow viscosity can be about 0.1 to about 30 Pa*s at a shear rate of 1/s, and is about 0.02 to about 0.8 Pa*s at a shear rate of 100/s. In additional embodiments, the flow viscosity is about 1 to about 10 Pa*s at a shear rate of 1/s, and is about 0.02 to about 0.5 at a shear rate of 100/s.

In further embodiments, the ECM hydrogel has a flow viscosity of about 10 to about 100 Pa*s at a shear rate of 0.1/s. In other embodiments, the ECM hydrogel has a flow viscosity of about 0.01 to about 0.2 Pa*s at a shear rate of 1000/s. In other embodiments, the ECM hydrogel has a flow viscosity of about 1 to about 40 Pa*s at a shear rate of 0.1/s and is 0.01 to 0.2 Pa*s at a shear rate of 1000/s.

The disclosed ECM hydrogels have a stiffness i) about 10 to about 400 Pascal (Pa), ii) about 10 to about 600 Pa, iii) about 5 to about 1,000 Pa, iv) about 10 to 1,000 Pa, or v) about 10 to about 70 Pa. The ECM hydrogel can have a stiffness of about 10 to about 300 Pascal (Pa), such as about 10 to about 70 Pa, about 10 to about 100 Pascal (Pa), or about 10 to about 150 Pa, about 10 to about 200 Pa, or about 10 to about 300 Pa. In some embodiments, the disclosed ECM hydrogels have a stiffness of about 10, 15, 20, 25, 30, 35, 40, 45, 50, 55, 60, 65, or 70 Pa. In other embodiments, the disclosed ECM hydrogels have a stiffness of about 10 to about 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 Pa. In further embodiments, the disclosed ECM hydrogel can have a stiffness of about 70, 75, 80, 85, 90, 95, 100, 110, 120, 130, 140, 150, 160, 170, 180, 190, 200, 210, 220, 230, 240, 250, 260, 270, 280, 290, or 300 Pa.

In some embodiments, the ECM concentration in the hydrogel is about 2 mg/ml to about 20 mg/ml, such as about 8 mg/ml to about 12 mg/ml or about 2 mg/ml to about 16 mg/ml. In other embodiments, the ECM concentration in the hydrogel is about 2, 3, 4, 5, 6, 7, 8, 9, 10, 11, 12, 13, 14, 15, or 16 mg/ml. Exemplary concentrations of use include, but are not limited to, about 9 mg/ml to about 11 mg/ml, and about 10 mg/ml to about 12 mg/ml. Additional exemplary concentrations include about 8 mg/ml to about 10 mg/ml, about 8 mg/ml to about 11 mg/ml, about 8 mg/ml to about 13 mg/ml, about 8 mg/ml to about 14 mg/ml, about 8 mg/ml to about 15 mg/ml, and about 8 mg/ml to about 16 mg/ml. Further exemplary concentrations of use also include about 6 mg/ml to about 12 mg/ml, about 13 mg/ml, about 14 mg/ml, about 15 mg/ml or about 16 mg/ml.

The disclosed ECM hydrogels can be provided as components of a kit. The ECM hydrogel can be provided in frozen or lyophilized form. In some embodiments, the kit can include the components needed to form the hydrogel, such as one container including the hydrogel, such as in a lyophilized form, one container including a solution for solubilizing the lyophilized hydrogel, and optionally a container comprising a neutralizing solution for neutralizing the solubilized form. In other embodiments, the kit can include a container including the solubilized hydrogel, and a second container including a neutralizing agent.

Optionally, such a kit includes additional components including packaging, instructions and various other reagents, such as buffers, substrates, or other therapeutic ingredients. The kit can include a container and a label or package insert on or associated with the container. Suitable containers include, for example, bottles, vials, syringes, etc. The containers may be formed from a variety of materials such as glass or plastic. The container typically holds a composition including the ECM hydrogel, such as in frozen or lyophilized form, which is effective for inhibiting esophageal inflammation and/or mitigating the effects of esophageal inflammation in a subject. In several embodiments, the container may have a sterile access port (for example the container may be an intravenous solution bag or a vial having a stopper pierceable by a hypodermic injection needle). The label or package insert indicates that the composition is used for endoscopic procedures for the particular condition, such as colorectal cancer.

The label or package insert typically will further include instructions for use. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed, such as needles or catheters. The kits may additionally include buffers and other reagents routinely used for the practice of a particular method. Kits and appropriate contents are well known to those of skill in the art.

Methods of Treatment

Methods are disclosed herein for dissecting a mucosa and a submucosa from a muscularis propria from a region of an organ of a subject, wherein the organ is not the esophagus. The organ can be in the gastrointestinal tract, for example, the duodenum, stomach, small intestine, large intestine (colon) or rectum The organ can be the bladder, organs of the oral-respiratory system (lungs, throat (pharynx), tongue, nasal passages, sinuses), the skin, or the uterus and vaginal tract. Examples of specific tissues are respiratory epithelium, nasal epithelium, dermal or epidermal tissue and uterine epithelium. The methods are of use in any organ that has a mucosa and a submucosa, wherein a superficial lesion can be formed, such as a malignant or pre-malignant lesion. The organ is not the esophagus.

These methods include injecting submucosally into the organ of the subject a pharmaceutical composition comprising an extracellular matrix (ECM) hydrogel to form a cushion between the submucosa and the underlying muscularis propria at the region of the organ, wherein the organ is not the esophagus. The method can be an endoscopic mucosal resection (EMR) or an endoscopic submucosal dissection (ESD).

EMR is an endoscopic technique developed for removal of sessile or flat neoplasms confined to the superficial layers (mucosa and submucosa) of the gastrointestinal (GI) tract. EMR is typically used for removal of lesions smaller than 2 cm or piecemeal removal of larger lesions. EMR also plays an important role in the assessment of resected specimens for accurate pathological staging. In contrast to polypectomy, EMR involves the lifting up of a lesion from the muscular layer by injecting a fluid agent, commonly normal saline (NS) solution, into the submucosal layer. EMR is also useful for obtaining specimens for accurate histopathological staging to determine the risk of lymph-node metastasis. EMR facilitates the complete removal of the affected mucosa by excising through the middle or deeper portion of the gut wall submucosa. Various EMR techniques have been described and four methods involving snare resection are commonly used: (1) the inject and cut method; (2) the inject, lift, and cut method; (3) cap-assisted EMR (EMRC); and (4) EMR with ligation (EMRL). In the inject and cut technique, the diseased mucosa is lifted up from the muscular layer by creating a submucosal fluid cushion, captured, strangulated using an electrosurgical snare, and then resected. However, injection into the thin submucosal layer is a delicate process, the injected solution tends to dissipate quickly, flat and depressed lesions are hard to capture with the snare compared with protruded lesions, and large or awkwardly located lesions can be difficult to remove (Uraoka et al., Drug Design, Development and Therapy 2008:2 131-138). Injection-assisted EMR is frequently used for large flat colon polyps.

Endoscopic submucosal dissection (ESD) was specifically developed for removing larger lesions. Lesions are dissected directly along the submucosal layer using an electrosurgical knife, resulting in an en-bloc resection of even large lesions. ESD has been predicted to replace conventional surgery in treating certain cancerous stages, but since it has a higher rate of perforation and bleeding complications than conventional EMR, a greater degree of endoscopic skill and experience is required than for EMR. ESD can use numerous electrosurgical knives, such as an insulation-tipped diathermic knife, a needle knife, a hook knife, a flex knife, a triangle tipped knife, a flush knife, splash needle, and a small-caliber tip transparent hood. These knives can be used with a high frequency electrosurgical current (HFEC) generator. ESD is characterized by three steps: (1) injecting a fluid to form a submucosal cushion to elevate the lesion from the muscle layer; (2) circumferential cutting of the surrounding mucosa of the lesion; and (3) dissection of the connective tissue of the submucosa beneath the lesion (see Kakushima et al., Wold J. Gstroenterol. 14(9): 2962-2967, 2008, incorporated herein by reference. Various submucosal injection solutions had previously been developed and shown to be satisfactory for use during EMR, but introduction of the lengthier ESD procedure required a longer-lasting solution to help identifying the cutting line during dissection of the submucosal layer (Uraoka et al., Drug Design, Development and Therapy 2008:2 131-138). The presently disclosed methods meet this need.

A submucosal injection is used in EMR, as injection of fluid into the submucosa cushions facilitates the isolation of the tissue to be removed just before capture of the target lesion, such as with a snare, thereby reducing thermal injury and the risk of perforation and hemorrhage while also facilitating resection. Submucosal injection plays an important role in the EMR procedure, as the solution must be retained in place for sufficient duration and needs to form a hemispheric shape to facilitate snaring. In addition, providing a sufficiently high submucosal elevation results in safe submucosal cutting during the ESD procedure (Uraoka et al., Drug Design, Development and Therapy 2008:2 131-138). Furthermore, as inflammation results from the procedure, any cushion retained at the procedure site should have anti-inflammatory properties. The ECM hydrogel will mitigate stricture and promote re-epithelialization. The presently disclosed methods also meet this need.

In some embodiments, the disclosed methods utilize an ECM hydrogel that has anti-inflammatory properties, and is inexpensive, non-toxic, easy to inject and provides a high, long-lasting submucosal cushion. The ECM hydrogel is administered in the pre-gel form, and then gels at the site of injection to form a cushion. The cushion can be dissected during the procedure so that some hydrogel remains on the underlying muscularis propria, thereby aiding healing. The disclosed ECM hydrogels facilitate closure of the wound created by removal of the resected mucosa/submucosa. In some embodiments, the procedure is an ESD. In other embodiments, the procedure is an EMR.

Normal saline solution (NS) and thinner solutions (e.g, ELEVIEW™, see U.S. Pat. No. 9,226,996, incorporated herein by reference) have been used as submucosal cushions for endoscopic resection, but the inherent characteristics of these solutions make it difficult to produce the proper submucosal fluid cushion, maintain the desired height, and retain the cushion at the desired location, because of the rapid dispersion of the solution. Furthermore, in ESD, once the mucosa/submucosa are removed, these agents will not be retained on the underlying muscularis propria. Furthermore, these agents to not aid the healing process, such as by reducing inflammation. The use of an ECM hydrogel meets these needs.

The ECM hydrogels disclosed herein can be used as in any ESD or ESR. As disclosed in U.S. Pat. No. 9,364,580, incorporated herein by reference, endoscopic injection needles are devices which can be long (up to about 230) cm and which include a relatively long catheter within which an inner injection tube having a distal injection needle is slideably disposed. A proximal actuating handle is coupled to the catheter and the injection tube for moving one relative to the other when necessary. Fluid access to the injection tube is typically provided via a leer connector on the handle. Endoscopic injection needle devices are typically delivered to the injection site through the working channel of the endoscope. In order to protect the lumen of the endoscope working channel from damage, the handle of the infusion needle device is manipulated to withdraw the distal injection needle into the lumen of the catheter before inserting the device into the endoscope. This prevents exposure of the sharp point of the injection needle as the device is moved through the lumen of the endoscope. When the distal end of the endoscopic injection needle device is located at the injection site, its handle is again manipulated to move the injection needle distally out of the lumen of the catheter. When advanced to the most distal position, the exposed portion of the injection needle is approximately 4-6 mm in length.

After the injection site has been pierced, the ECM in pre-gel form, usually contained in a 5 ml to 10 ml syringe provided with a luer-lock fitting connected to the handle of the injection needle, can be delivered through the injection tube and the needle into the injection site, such as between the submucosa and the underlying muscularis propria.

The injection needle and other accessories commonly used during endoscopic procedures, such as snares for polypectomy, clipping devices, biopsy forceps and similar, are passed through one or more specific channels of the endoscope, usually called working channels or operating channels. Depending upon the type of endoscope used in GI endoscopy (e.g. gastroscope, enteroscope, colonoscope, duodenoscope, sigmoidoscope and similar), the inner diameter of the working channels may vary considerably. However, the most common endoscopes used in GI endoscopy have working channels with inner diameter in the range from about 2 mm to about 5 mm. Generally, the manufacturers of endoscopic accessories produce accessories having outer diameters which allow them to fit all the working channels. In some embodiments, the endoscopic injection needles, the outer diameter of catheter ranges from 1.9 mm to 2.3 mm, such as about 1.9, 2.0, 2.1, 2.2 or 2.3 cm. Thus, considering that the inner injection tube is contained in the outer catheter, its internal diameter is usually 1 mm or less. The disclosed ECM hydrogels, in the pre-gel form, can readily pass through these catheters.

The ECM hydrogel, in pre-gel form, can be used in an endoscopic resection procedure by sucking a volume of emulsion from its primary container by means of a syringe, injecting a suitable volume of said emulsion by means of an endoscopic injection needle inserted in the working channel of the endoscope immediately under the superficial mucosal layer, to depose a liquid volume into the submucosal layer that becomes a cushion when in place: the elevation of the mucosal surface allow the endoscopist to perform an easy resection of the mucosal lesion found during the execution of the endoscopic procedure even if the lesion is flat and thus not protruding into a lumen, such as an intestinal or gastric lumen.

The presence of at least one dye into the cushion can aid an endoscopist to visualize the structures beneath the mucosa (e.g. the submucosal layer and the external muscular wall), thereby lowering the risk that the endoscopist, performing the resection procedure, may cause damages to said structures. The use of the dye can allow visualization of the cushion cavity and the mucosal basement. The removal of the lesion from the mucosal surface generates a mucosal wound. The persistence of the cushion generated by the injected volume of the pharmaceutical composition allows the endoscopic resection procedure to be performed without the need to re-inject. The ECM hydrogel in pre-gel form is injected submucosally into a region of interest in the organ of the subject, such as at the region of a lesion or tumor, to form a cushion between the submucosa and the underlying muscularis propria at the region of the organ. The cushion can be dissected, such that a portion of the ECM hydrogel is maintained on the underlying muscularis propria and aid in the healing process.

The organ can be any organ of interest, such as an organ of the gastrointestinal tract. The organ is not the esophagus. The organ may be in the upper gastrointestinal tract such as the pharynx, tongue or mouth. The organ may be the bladder, vaginal tract, or uterus. In some embodiments, the organ is the colon, duodenum, stomach, cecum, colon, sigmoid colon, rectum, small intestine or large intestine. In one non-limiting example, the organ is the stomach, the small intestine or the large intestine, and the method comprises a method of dissecting a carcinoma or adenocarcinoma from the stomach. In a further non-limiting example, the organ is the colon, and wherein the method comprises dissecting a polyp or a carcinoma from the colon.

An ECM hydrogel, as disclosed herein, is maintained at a temperature at or below which it gels, such as at or below room temperature (e.g., about 25° C.). The ECM hydrogel can be maintained, for example, at 25° C. or 4° C. prior to administration. An effective amount of the ECM hydrogel, in the pre-gel form, is then utilized The ECM hydrogel gels in the tissue of the subject, which is at a temperature of approximately 37° C. The ECM hydrogel can be provided in in a lyophilized or frozen form, and reconstituted just prior to administration to the region of the organ in the subject.

The disclosed methods are of use in any subject, including human and veterinary subjects. The subject can be any age. The subject can be an adult or a juvenile. In one embodiment, a composition including an ECM hydrogel, in pre-gel form, is injected in a target tissue in an organ to form a cushion which is then optionally subjected to an endoscopic surgical procedure, such as a resection procedure. The ECM can be from the same species as the subject being treated, or can be from a different species. In some embodiments, the subject is human, and the ECM hydrogel is derived from human or porcine ECM. In other embodiments, the ECM hydrogel is derived from a non-human primates, dog, cat, horse, or cow. The ECM can also be from a commercial source. The ECM hydrogel can, in some embodiments, be derived from any mammalian tissue, such as but not limited to porcine or human tissue, and be, in some non-limiting examples, urinary bladder, small intestine, or the esophagus. Any of the ECM hydrogels disclosed above can be used as a submucosal cushion, and/or in any of the disclosed methods. The hydrogel can be an esophageal ECM hydrogel or a urinary bladder hydrogel.

The disclosed methods are invasive, as they require an injection that dissects a mucosa and a submucosa from a muscularis propria from a region of an organ of an intestinal tract of a subject. Thus, the ECM is not applied to a surface of an organ, such as an organ of the gastrointestinal tract. The disclosed methods are not practiced on the esophagus.

Any of the methods disclosed herein can include injecting submucosally into the organ of the subject a pharmaceutical composition including an extracellular matrix (ECM) hydrogel to form a cushion between the submucosa and the underlying muscularis propria at the region of the organ. The ECM hydrogel has the following characteristics: a) a time to 50% gelation of less than 30 minutes at a temperature of about 37° C.; b) a flow viscosity suitable for infusion into the organ; and c) a stiffness of about 10 to about 400 Pascal (Pa). The method can utilize any of the hydrogel disclosed above. The ECM hydrogel gels and dissects the mucosa and the submucosa from the underlying muscularis propria and inhibits inflammation in the region of the organ in the subject. The ECM hydrogel, in pre-gel form, can be administered endoscopically or via a catheter. In some embodiments, the organ is the colon, stomach, cecum, colon, sigmoid colon, rectum, small intestine or large intestine.

In some embodiments, the resection procedure is an endoscopic mucosal resection or an endoscopic submucosal dissection. In further embodiments, the organ is the stomach, small intestine or large intestine, and the method comprises a method of dissecting a polyp, a carcinoma or an adenocarcinoma from the colon. In more embodiments, the method includes dissecting the mucosa and the submucosa from an organ of a patient who has dysplasia. In specific non-limiting examples, the method comprises dissecting a polyp or a carcinoma from the colon. Generally, the organ is not the esophagus.

The methods can also include performing an endoscopic resection procedure on the cushion. In some embodiments, the methods include dividing the cushion such that hydrogel is retained on the underlying muscularis propria of the organ and the mucosa and the submucosa are removed from the region of the organ.

In some embodiments, the time to 50% gelation of the hydrogel is than 30 minutes at a temperature of about 37° C. In some specific non-limiting example, the time to 50% gelation is about 2 to about 30 minutes at about 37° C. In other specific non-limiting examples, the time to 50% gelation is about 2 to about 10 minutes at about 37° C. In further non-limiting examples, the time to 50% gelation is about 3 to about 10 minutes.

In additional embodiments, the flow viscosity in pre-gel form is sufficient for injection into an organ of interest. In some embodiments, the flow viscosity of the ECM hydrogel is flow viscosity is about 0.1 to about 100 Pa*s at a shear rate of about 0.1/s and is about 0.01 to about 0.2 Pa*s at a shear rate of 1000/s. In some non-limiting examples, the flow viscosity is about 30 Pa*s at a shear rate of 1/s, and is about 0.02 to about 0.8 Pa*s at a shear rate of about 100/s.

In further embodiments, ECM hydrogel has stiffness when introduced into the tissue of about 10 to about 300 Pascal (Pa); wherein the ECM hydrogel has a stiffness of 10-70 Pa. In further embodiments, the ECM concentration in the hydrogel is 2 mg/ml to about 16 mg/ml.

The ECM hydrogel can be produced by any method disclosed herein. In some embodiments, the ECM hydrogel is produced by (a) solubilizing decellularized extracellular matrix (ECM) by digestion of tissue with an acid protease in an acidic solution to produce digested ECM; and (b) raising the pH of the digested ECM to a pH between 7.2 and 7.8 to produce a neutralized digest solution. In further embodiments, step (b) raising the pH of the digested ECM includes adding a base or an isotonic buffer to raise the pH of the digested ECM. In further embodiments, an acid protease is used, such as pepsin, trypsin or a combination thereof. The ECM hydrogel can be an esophageal ECM hydrogel. The ECM hydrogel can be a urinary bladder ECM hydrogel.

In some embodiments, the ECM hydrogel is maintained at or below 25° C. prior to administration to the subject. In some embodiments, the ECM hydrogel is maintained at about 4° C. to about 28° C., such as about 4, 5, 6, 7, 8, 9, 10, 11, 12, 13, 14, 15, 16, 17, 18, 19, 20, 21, 22, 23, 24, 25, 26, 27 or 28° C. The ECM hydrogel can be maintained at about 4° C., and used at about 4° C. to about 25° C., or warmed to just about 25° C., just prior to use. In some embodiments, controlling temperature ensure that the ECM hydrogel is maintained in its pre-gel form, and thus is suitable for injection between the submucosa and the underlying muscularis propria. In further embodiments, the hydrogel gels upon administration to the subject, such as when reaching a temperature of, for example, 37° C.

EXAMPLES

ELEVIEW™ and ECM hydrogels are different biomaterials. ELEVIEW™ (Aries Pharmaceuticals, Inc, Dublin, Ireland) is a commercially available low viscosity emulsion of Poloxamer 188 clinically used to provide submucosal lift for EMR and ESD procedures. It is disclosed herein that ELEVIEW™ does not form a stably formed hydrogel at 37° C., but rather remains a liquid over an hour at 37° C. In contrast, 12 mg/mL of an esophageal ECM hydrogel (eECM) (prepared according to the method disclosed herein, i.e., by protease digestion of ECM) forms a hydrogel that is stably formed at 37° C. (body temperature). ELEVIEW™ and eECM can be injected underneath the mucosa. An ideal biomaterial would adhere to both layers. There was no difference in mucoadhesive strength between ELEVIEW™ and eECM 12 mg/mL to the muscle. Surprisingly, eECM had a stronger mucoadhesion than ELEVIEW™ to the mucosa. Furthermore, eECM demonstrated biological activity by macrophage polarization towards a remodeling phenotype. This demonstrates that an extracellular matrix hydrogel can be effectively used as a submucosal cushion, and thus can be used to dissect the submucosa from the underlying muscularis propria.

Example 1

Materials and Methods

Rheology

The viscoelastic properties of ELEVIEW™ and eECM 12 mg/mL were determined with a temperature-controlled, 40 mm parallel plate rheometer (AR2000). The samples were kept at 4° C. and loaded onto the rheometer with a parallel plate geometry pre-cooled to 10° C. Mineral oil was used to seal the sample-plate interface and to minimize evaporation during the testing. A series of rheological tests were conducted for each sample in sequence. A steady state flow curve at 10° C. was performed to determine the viscosity profile of the samples at a range of shear rates (0.1-1000 s$^{-1}$). Plate temperature was rapidly raised from 10° C. to 37° C., and an oscillatory time sweep was performed at 37° C., by applying a small, 0.5% oscillatory strain at a frequency of 1 rad/s to measure the maximum storage modulus (G'), maximum loss modulus (G") and gelation kinetics. Data was extracted and analyzed in Prism (Version 6, GraphPad) for statistical analysis (n=3).

Muco-Adhesion to Muscularis

Porcine mucosa and muscularis were mechanically isolated by stripping the mucosa and submucosa from the underlying muscularis layer. ELEVIEW™ and eECM (12 mg/mL) were pipetted in a 6 well plate. The mucosa or muscularis were glued to the bottom surface of a half-sphere (40 mm diameter) that rests on top of ELEVIEW™ or eECM, such that the surface area of the mucosa or muscularis in contact with ELEVIEW™ or eECM remains constant for all tests. The construct was incubated for 1 h at 37° C. for adherence to the mucosa or muscularis. After 1 h, the construct was placed on the MTS Insight Tensile machine with 10N load cell and ball burst attachment, set to a measuring frequency of 10 Hz. The ball burst attachment was securely attached to the half-sphere and the half-sphere was raised up at 5 mm/min. The maximum force value was considered the adhesion force, subtracted by the force of the freely hanging construct. Measurements were only accepted if the detachment occurred between the mucosa or muscularis and the hydrogel (n=3).

Ex-Vivo Submucosal Fluid Cushion Performance

Porcine colon and stomach were placed in a 37° C. incubator and their temperature was monitored with a thermometer until tissues reached 37° C. After reaching the target temperature, a 23G needle was used to inject 2 mL of either ELEVIEW™ or neutralized eECM at 12 mg/mL in the submucosa. eECM was kept on ice during the procedure. Tissues were evaluated and photographed alongside a metric witness at 15 minutes intervals for up to 75 minutes. Tissues were kept incubated at 37° C. throughout the procedure. After 75 minutes, the area injected with the test agents was dissected and evaluated. ImageJ was used to quantify the elevation of the mucosa after injection of the agent throughout the experiment.

Macrophage Isolation and Activation

Mouse bone marrow was harvested as previously described [1, 2]. Briefly, female 6 to 8 week old C57bl/6 mice (Jackson Laboratories, Bar Harbor, ME) were euthanized via CO2 inhalation and cervical dislocation. Aseptically, the skin from the proximal hind limb to the foot was removed, the tarsus and stifle disarticulated, and the tibia isolated. The coxafemoral joint was disarticulated for isolation of the femur. After removal of excess tissue, bones were kept on ice and rinsed in a sterile dish containing macrophage complete medium consisting of DMEM (Gibco, Grand Island, NY), 10% fetal bovine serum (FBS) (Invitrogen, Carlsbad, CA), 10% L929 supernatant[2], 50 uM beta-mercaptoethanol (Gibco), 100 U/ml penicillin, 100 ug/ml streptomycin, 10 mM non-essential amino acids (Gibco) and 10 mM hepes buffer. The ends of the bones were transected and the marrow cavity was flushed with complete medium to collect bone marrow. Cells were washed, plated at 2×106 cells/ml, and allowed to differentiate into macrophages for 7 days at 37° C., 5% CO2 with complete media changes every 48 hours as previously described [3]. After 7 days, resulting naïve macrophages were treated with basal media consisting of 10% FBS, 100 ug/ml streptomyocin, 100 U/ml penicillin in DMEM and one of the following conditions as previously described: (1) 20 ng/ml IFNγ and 100 ng/ml of LPS to promote an M1-like phenotype, (2) 20 ng/ml IL-4 to promote an M2-like phenotype, (3) 250 ug/ml of pepsin control buffer, (4) 250 ug/ml of esophageal ECM, or (5) same volume of ELEVIEW™ for 24 hours at 37° C., 5% CO2[4].

Immuno-Labeling of Macrophages

After 24 hours, macrophages were washed and fixed with 2% paraformaldehyde. Following PBS washes, cells were incubated in blocking solution consisting of 0.1% Triton-X 100, 0.1% Tween 20, 4% normal goat serum, and 2% bovine serum albumin (BSA) for 1 hour at room temperature to prevent non-specific antibody binding. The following primary antibodies were diluted in blocking solution: (1) monoclonal anti-F4/80 (Abcam, Cambridge, MA) at 1:100 dilution for a pan-macrophage marker, (2) polyclonal anti-iNOS (Abcam, Cambridge, MA) at 1:100 dilution for an M2 marker, (3) polyclonal anti-Fizz1 (Peprotech, Rocky Hill, NJ) at 1:100 dilution for an M2 marker, (4) polyclonal to liver Arginase (Abcam, Cambridge, MA) at 1:100 dilution for an M2-like marker [5-7]. Cells were incubated in primary antibodies for 16 h at 4° C. After PBS washes, cells were incubated in fluorophore-conjugated secondary antibodies (Alexa Fluor goat anti-rat 488 or goat anti-rabbit 488, Invitrogen) for 1 hour at room temperature. After PBS washes, nuclei were counterstained with 4'6'diamidino-2-phenylindole (DAPI) prior to imaging three 200× fields using a live-cell microscope. Light exposure times were standardized to a negative isotype control and kept constant across images. Images were quantified utilizing CellProfiler Image Analysis software to obtain positive F4/80, iNOS, Fizz1, and Arginase1 percentages.

In-Vivo Use of ECM as Submucosal Fluid Cushion for EMR

Anesthesia is induced with Acepromazine (0.01 mg/kg, SC) and ketamine (5-11 mg/kg), and surgical plane anesthesia is maintained with 1-5% Isofluorane via endotracheal tube. Throughout the procedure and immediate post-operative period, animals are administered 2 ml/kg/h of lactated Ringer's solution I.V. Temperature is controlled through warm water recirculating heating pads placed under the animal. Physiologic parameters such as heart, respiration rate, body temperature, and responsiveness are monitored during the procedure. Antibiotic prophylaxis with 25 mg/kg of Cefazolin is administered before starting the procedure.

The animal is placed in supine position with and a Pentax EG3430K endoscope is used to evaluate the organ. After identifying reference points in the organ, the mucosa and submucosa at the site of excision were separated by with injection blue-dyed Urinary Bladder Matrix—hydrogel at 8 mg/ml using an Olympus Injectorforce 4 mm 23G needle. at 4° C. This temperature is maintained at all times to prevent gelation and potential plugging of the needle. Approximately 2-5 ml of blue gel is injected per site. The full circumference of the mucosa (100%) for a length of 5 cm is removed using band-ligation EMR technique. For EMR a Cook Duette Kit with a ligation band is used. The mucosa is then excised with the use of a snare.

Statistics

A 2-way ANOVA was used to compare the effect of the independent variables shear rate and sample on the dependent variable viscosity; and also to compare the effect of the independent variables sample and modulus type on the dependent variable modulus. A Sidak post-hoc multiple comparisons test was used and significance was determined using the 95% confidence interval and p-values were adjusted for multiple comparisons. A t-test was performed for the mucoadhesive strength comparing ELEVIEW™ and eECM 12 mg/mL.

Example 2

Viscoelastic Properties

Figure 1B:
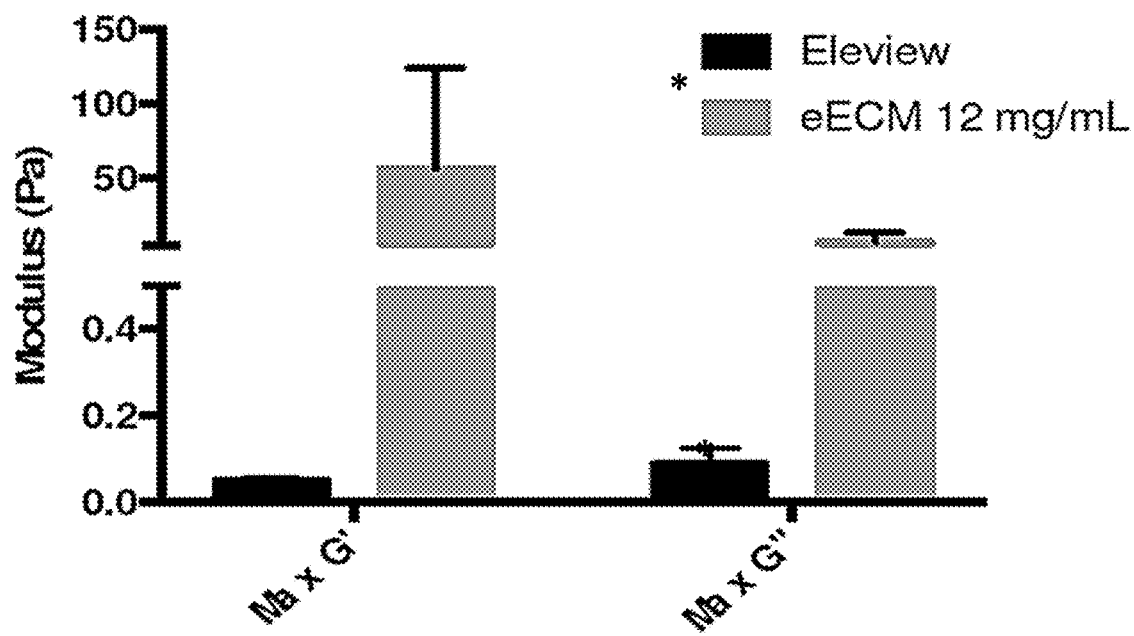
Figure 1C:
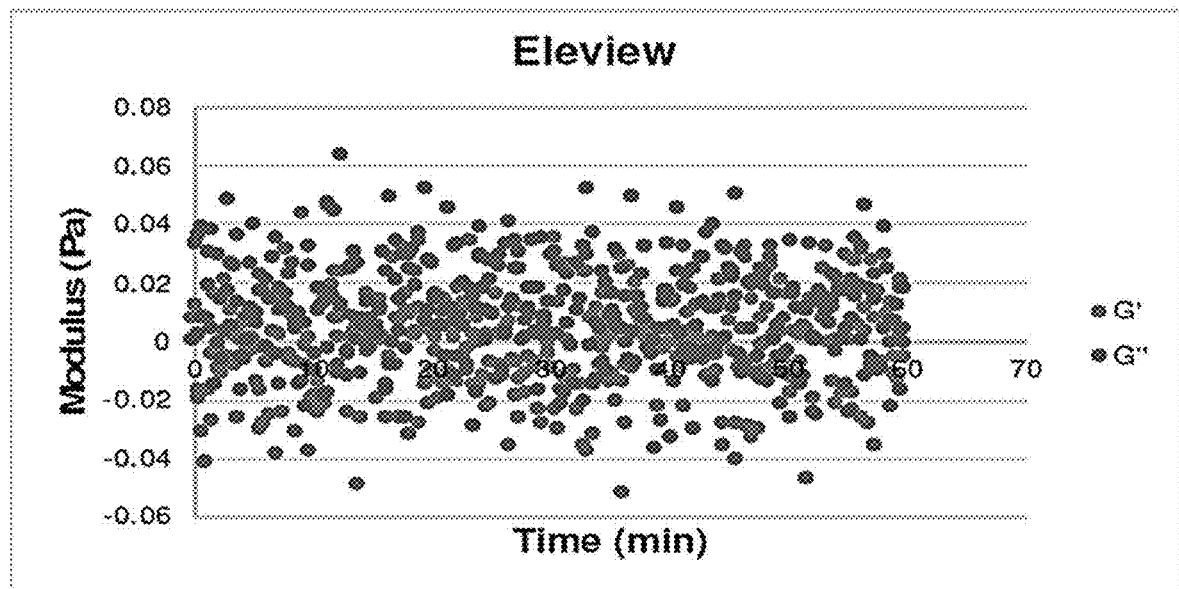
Figure 1D:
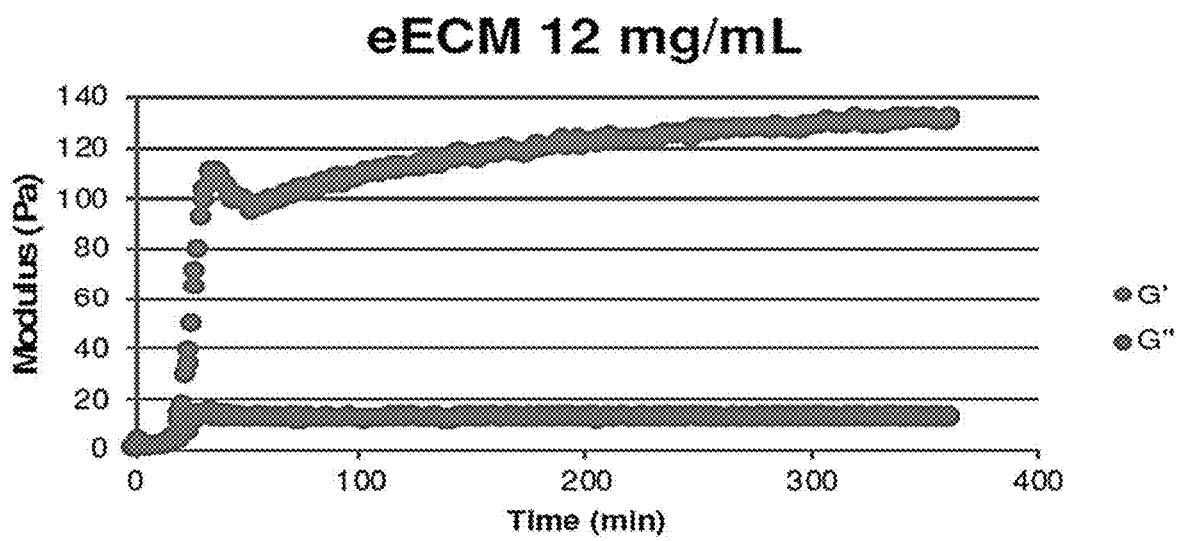
Figure 1E:
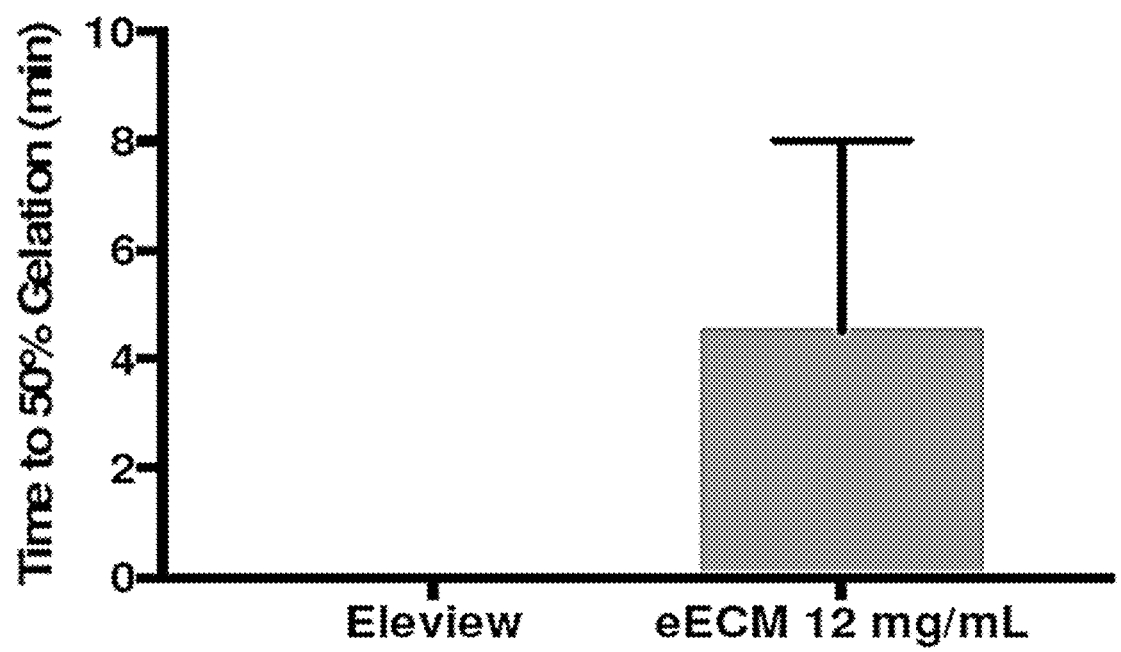

ELEVIEW™ was significantly less viscous than eECM 12 mg/mL at 0.1 1/s shear rate (p<0.0001), and trended towards being less significant at 1 1/s (p=0.054) (FIG. 1A). ELEVIEW™ did not form a stably formed hydrogel because the loss modulus (G") average (0.09±0.04 Pa) is greater than the storage modulus (G') average (0.05±0.01 Pa), while eECM 12 mg/mL has a storage modulus (G') (56.95±66.72 Pa) that is~order of magnitude greater than the loss modulus (G") (7.62±6.30 Pa) following the definition of a stably formed ECM hydrogel (Freytes et al., Biomaterials, 2008. 29(11): p. 1630-7) (FIG. 1B). The representative graphs of the time sweep of ELEVIEW™ further demonstrate that ELEVIEW™ does not form a hydrogel (FIG. 1C), while the eECM 12 mg/mL storage modulus increases sigmoidally and plateaus over time (FIG. 1D). Therefore, the gelation time to 50% gelation could be calculated for eECM 12 mg/mL (4.5±3.5 min), but not for ELEVIEW™ (FIG. 1E).

Example 3

Mucoadhesive Force to the Muscularis

Figure 2A:
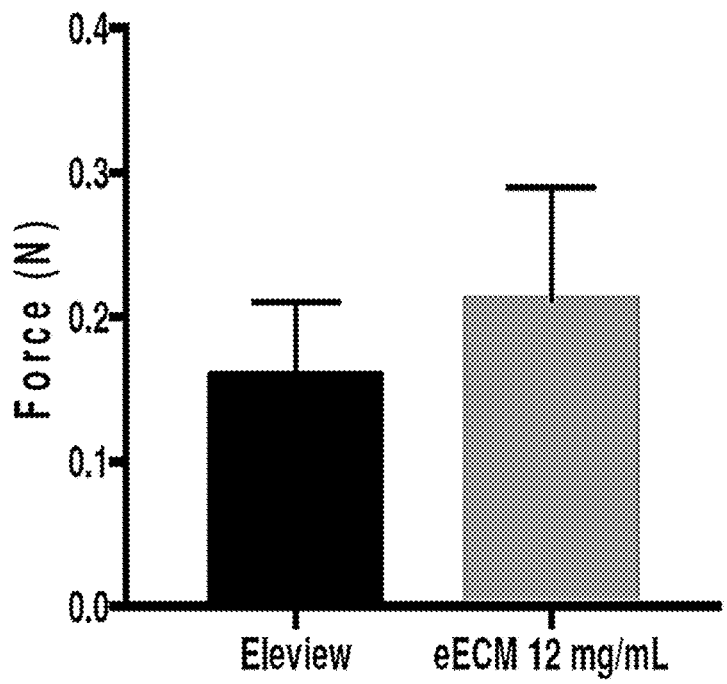
FIGS. 2A-2B. Mucoadhesive strength. The mucoadhesive strength of ELEVIEW™ and eECM 12 mg/mL to porcine muscularis (A) or mucosa (B).
Figure 2B:
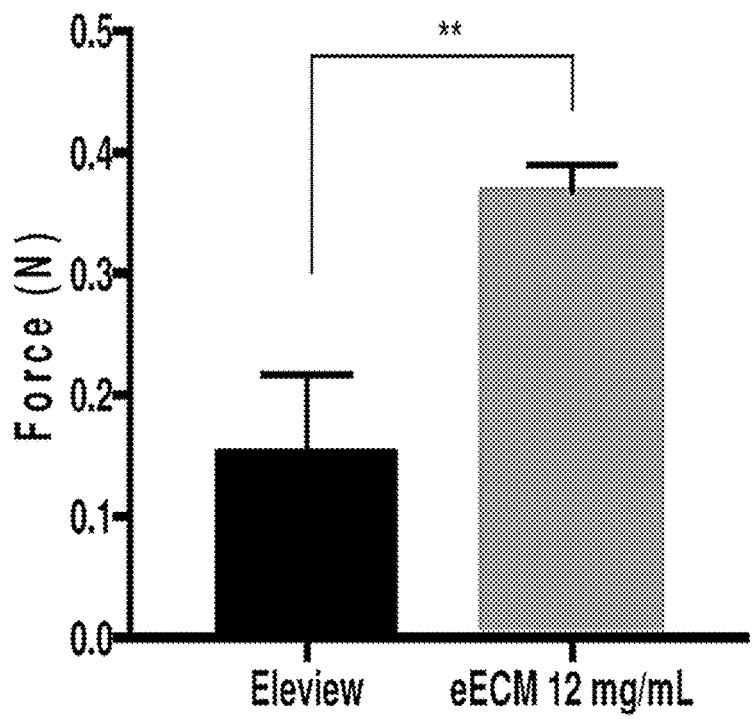

ELEVIEW™ (0.16±0.05 N) and eECM (0.21±0.08 N) did not show significantly different mucoadhesion to the muscularis (FIG. 2A). eECM had a higher mucoadhesive strength to the mucosa (0.37±0.02 N) than ELEVIEW™ (0.15±0.06 N) (p=0.0053) (FIG. 2B).

Example 4

Macrophage Activation

Figure 3:
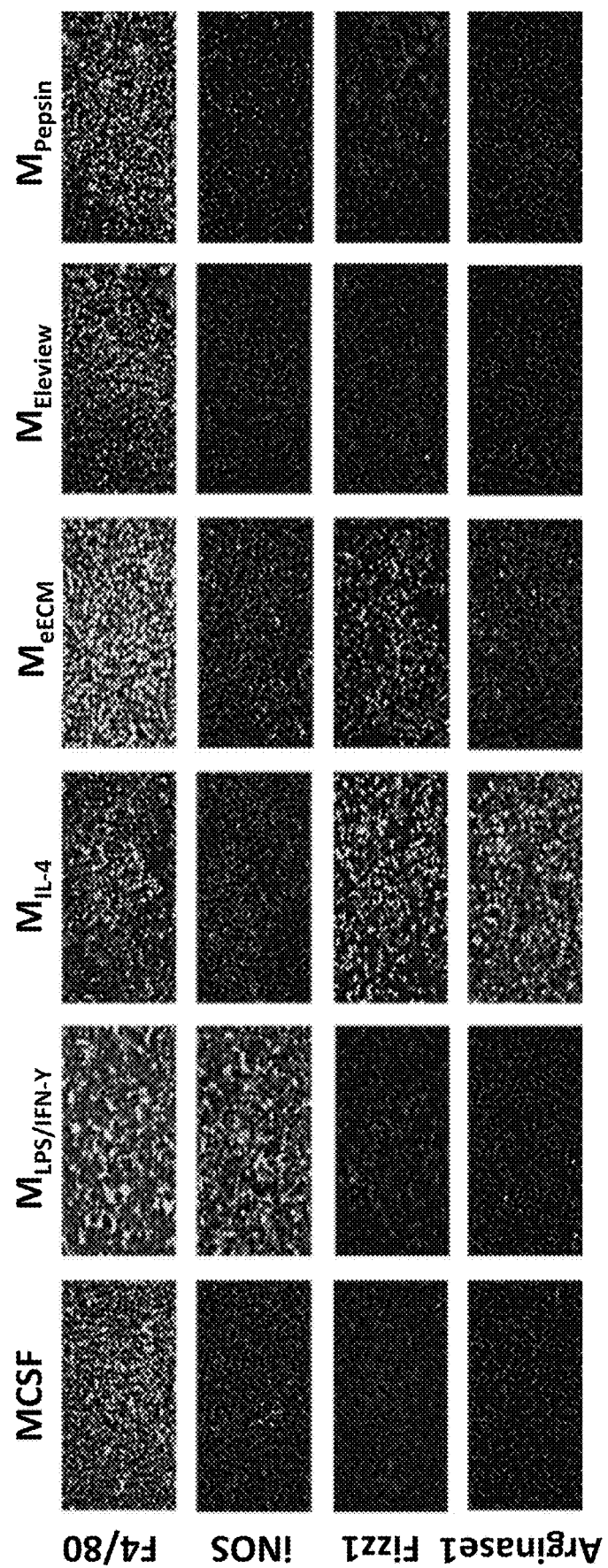
FIG. 3. Macrophage activation. Macrophage expression of anti-inflammatory and pro-inflammatory markers after exposure to eECM and ELEVIEW™.

Macrophages exposed to eECM showed activation of FIZZ1, an anti-inflammatory marker with minimal iNOS expression (a pro-inflammatory marker). iNOS expression was comparable between ELEVIEW™, eECM and carrier (Pepsin) control (FIG. 3). ELEVIEW™ did not show any bioactivity.

Example 5

Ex-Vivo Submucosal Fluid Cushion Performance

Figure 4A:
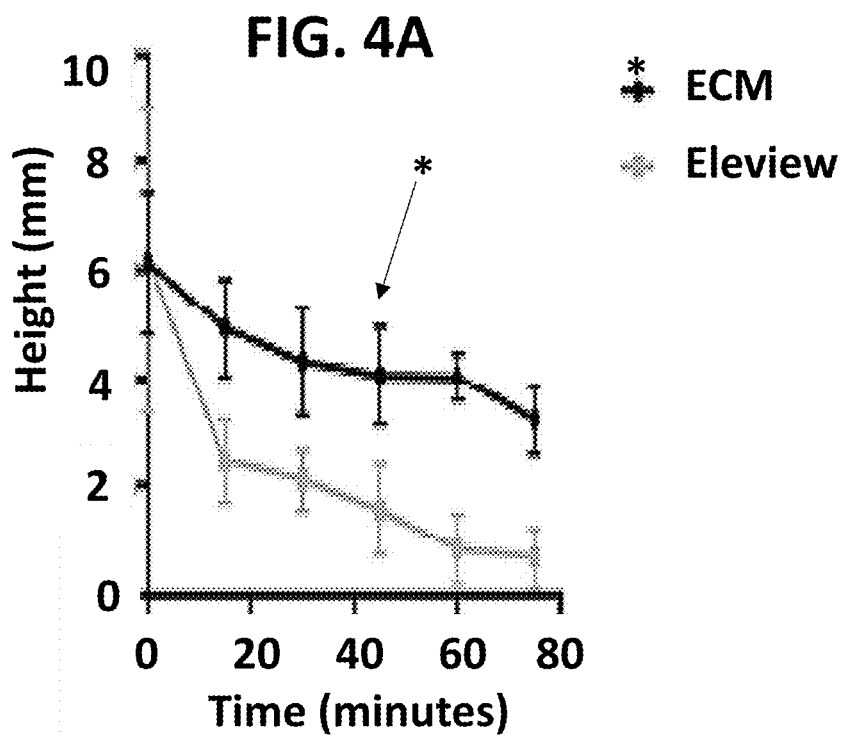
FIGS. 4A-4C. Submucosal fluid cushion—Colon. Measurements of elevation of submucosal fluid cushion over time with ECM (eECM) compared to ELEVIEW™ (A). Appearance of tissue after injection of 2 mL of test agent after injection and after 75 minutes (B). Dissection and exposure of test agent after 75 minutes (C).
Figure 4B:
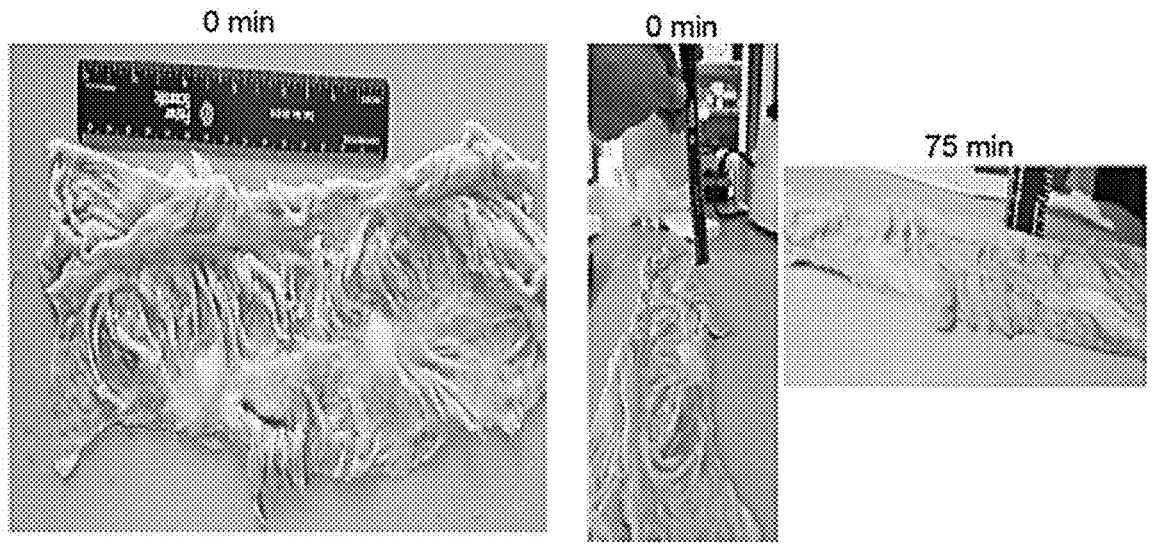
Figure 4B:
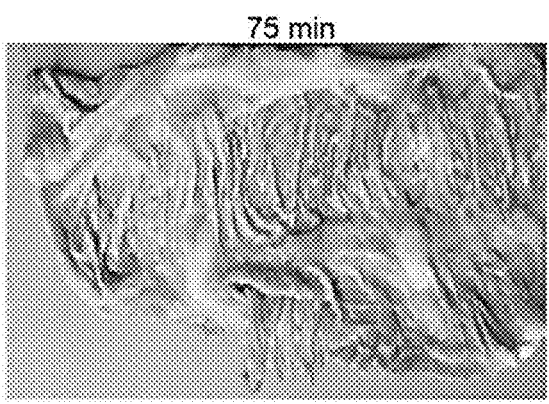
Figure 4C:
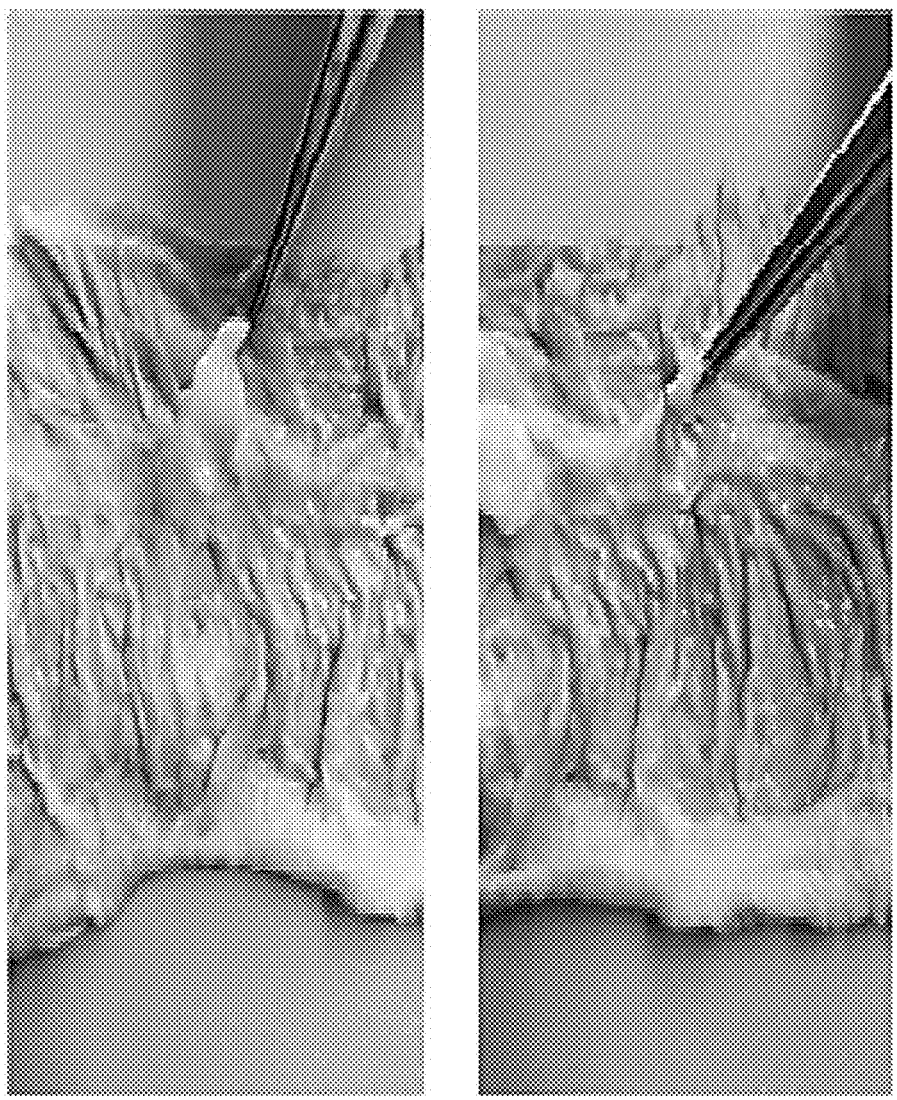
Figure 5A:
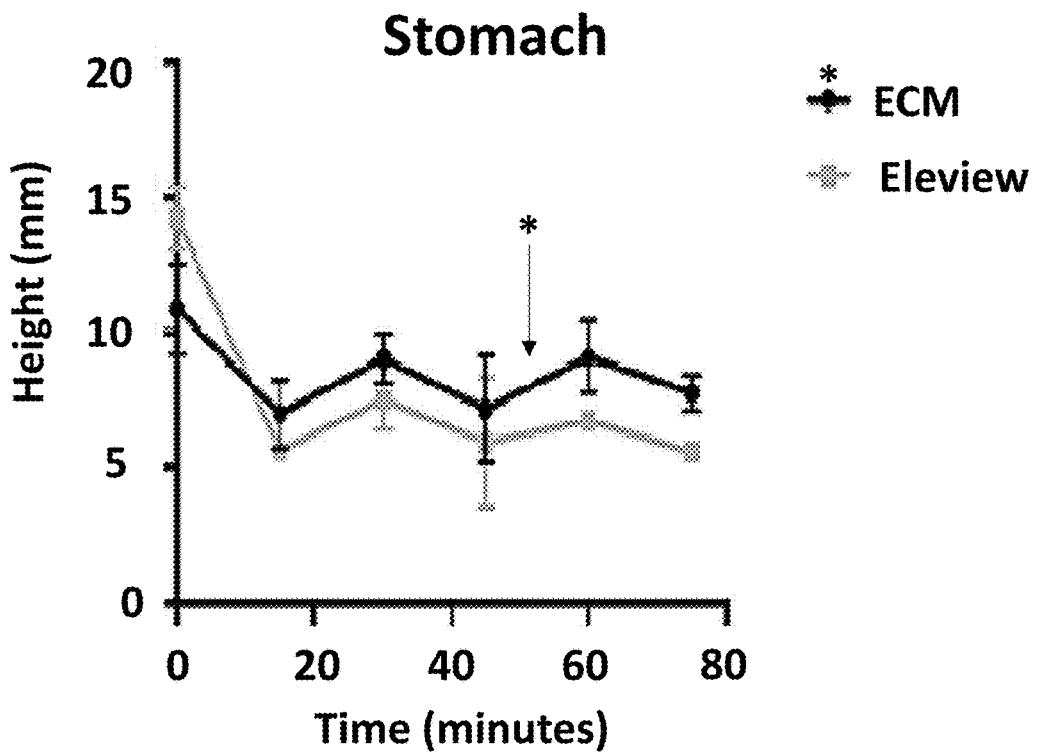
FIGS. 5A-5C. Submucosal fluid cushion—Stomach. Measurements of elevation of submucosal fluid cushion over time with eECM or ELEVIEW™ (A). Appearance of tissue after injection of 2 mL of test agent after injection and after 75 minutes (B). Dissection and exposure of test agent after 75 minutes.
Figure 5B:
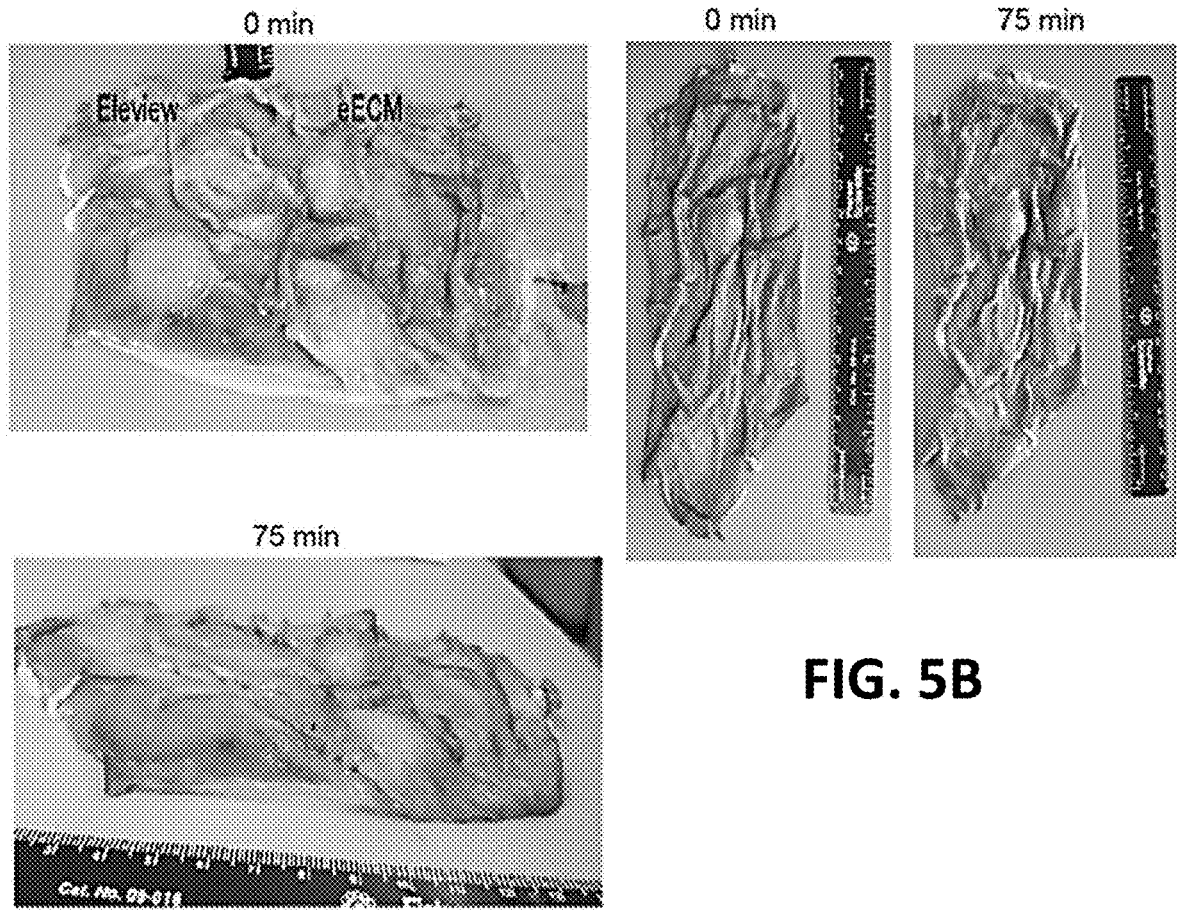

ELEVIEW™ and eECM successfully created a fluid cushion with injection of 2 mL of test agent into the colon (FIG. 4) or stomach (FIG. 5). The two test agents were easily injectable with a 23G needle. ELEVIEW™ appeared to diffuse since the moment of injection. Measurements and macroscopic appearance of the cushion height confirmed this observation (FIGS. 4A, 4B, 5A, 5B) for the two tissues tested. Colon and stomach had the larger loss of cushion height from 0 to 15 minutes (FIGS. 4A, 5A). The loss of cushion height was greater for ELEVIEW™ than for eECM. The decrease in cushion height continued for both test agents, however it was clear that the loss was greater for ELEVIEW™ in the colon. The stomach, however had a similar loss of cushion height for both test agents (FIG. 5A).

Figure 5C:
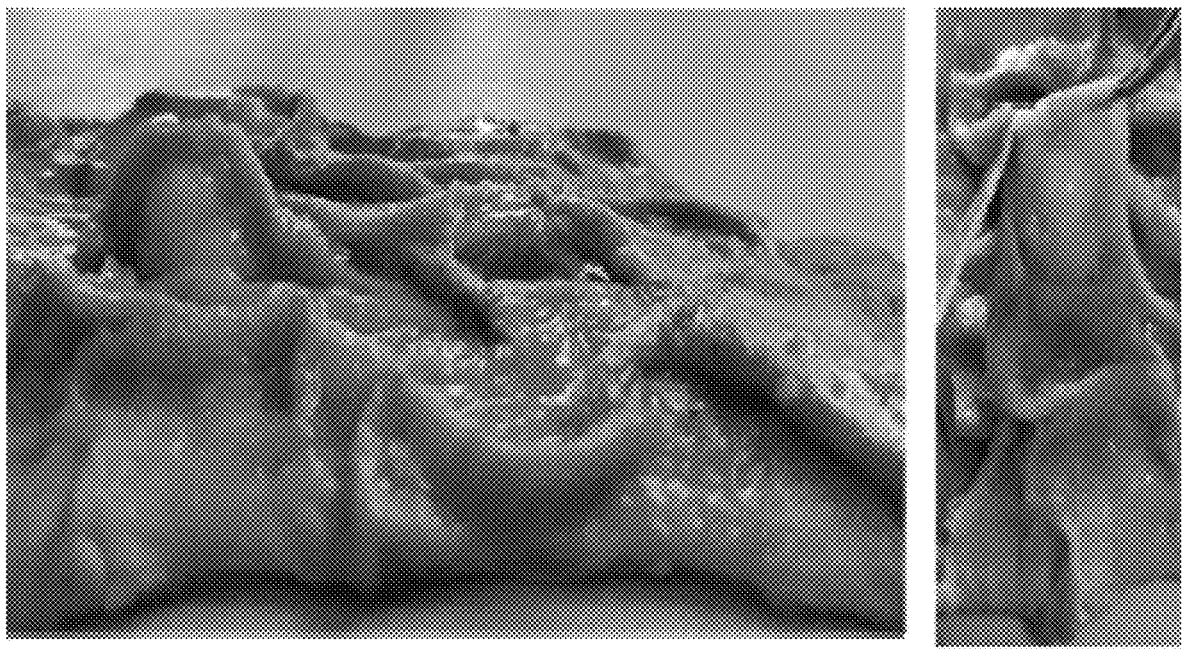

Dissection after 75 minutes showed differences between ELEVIEW™ and eECM in all tissues. Areas injected with ELEVIEW™ showed viscous liquid with no clear adhesion to the mucosa or underlying muscle layer. Areas previously injected with eECM showed clear and defined mass of gel that remained and adhered to the mucosa and underlying muscle. (FIGS. 4C, 5C). This aligns with the above results (see Example 2) that demonstrated that ELEVIEW™ is not capable of forming a gel (FIG. 1D).

Example 6

In-Vivo Use of ECM as Submucosal Fluid Cushion for EMR

The ECM-hydrogel is deliverable through a long endoscopic needle without any resistance. Elevation of the mucosa is successfully achieved and maintained to facilitate the EMR procedure and the blue dye was visible indicating the places were the dissection had been created for removal. Tissue is removed with the use of the snare. Upon macroscopic observation, the removed mucosal tissue includes part of the gel. The blue dye in the hydrogel appears to diffuse across the circumference of the organ after removing the mucosa and a full-circumferential is achieved with the use of the hydrogel.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for dissecting a mucosa and a submucosa from a muscularis propria from a region of an organ of a subject, comprising:
    injecting submucosally into the organ of the subject a pharmaceutical composition comprising an extracellular matrix (ECM) hydrogel to form a cushion between the submucosa and the underlying muscularis propria at the region of the organ, thereby dissecting the mucosa and the submucosa from the underlying muscularis propria and inhibiting inflammation in the region of the organ in the subject, wherein the organ is not the esophagus, and wherein the ECM hydrogel has the following characteristics:
    a) a time to 50% gelation of less than 30 minutes at a temperature of about 37° C.;
    b) a flow viscosity suitable for infusion into the organ;
    c) a stiffness of about 10 to about 400 Pascal (Pa); and
    d) an ECM concentration of about 8 mg/ml to about 20 mg/ml.

2. The method of claim 1, wherein the time to 50% gelation is less than 20 minutes at a temperature of about 37° C.

3. The method of claim 1, wherein the time to 50% gelation is about 3 to about 10 minutes.

4. The method of claim 1, wherein the flow viscosity is about 0.1 to about 100 Pa*s at a shear rate of about 0.1/s and is about 0.01 to about 0.2 Pa*s at a shear rate of 1000/s.

5. The method of claim 1, wherein the flow viscosity is about 0.1 to about 30 Pa*s at a shear rate of 1/s, and is about 0.02 to about 0.8 Pa*s at a shear rate of about 100/s.

6. The method of claim 1, wherein the ECM hydrogel has a stiffness of 10-300 Pa.

7. The method of claim 1, wherein the ECM hydrogel is an esophageal ECM hydrogel.

8. The method of claim 1, wherein the ECM concentration in the hydrogel is about 8 mg/ml to about 16 mg/ml.

9. The method of claim 1, wherein the ECM hydrogel is administered endoscopically or via a catheter.

10. The method of claim 1, wherein the ECM hydrogel is produced by
    (a) solubilizing decellularized extracellular matrix (ECM) by digestion with an acid protease in an acidic solution to produce digested ECM; and
    (b) raising the pH of the digested ECM to a pH between 7.2 and 7.8 to produce a neutralized digest solution.

11. The method of claim 10, wherein (b) raising the pH of the digested ECM comprises adding a base or an isotonic buffer to raise the pH of the digested ECM.

12. The method of claim 10, wherein the acid protease is pepsin, trypsin or a combination thereof.

13. The method of claim 1, wherein the ECM hydrogel is maintained at or below 25° C. prior to administration to the subject.

14. The method of claim 1, wherein the ECM hydrogel is injected endoscopically or via a catheter.

15. The method of claim 1, wherein the ECM hydrogel is prepared from ECM derived from urinary bladder, small intestine, dermis, kidney, or liver.

16. The method of claim 1, wherein the organ is the colon, stomach, cecum, sigmoid colon, rectum, small intestine or large intestine.

17. The method of claim 16, wherein the organ is the colon and the method comprises dissecting the mucosa and the submucosa from the colon.

18. The method of claim 16, wherein the organ is the colon, and wherein the method comprises dissecting a polyp or a carcinoma from the colon.

19. The method of claim 1, wherein the organ is the stomach, small intestine or large intestine, and the method comprises a method of dissecting an adenocarcinoma or carcinoma from the organ.

20. The method of claim 1, further comprising performing an endoscopic resection procedure on the cushion to remove the dissected mucosa and submucosa.

21. The method of claim 20, wherein the resection procedure is an endoscopic mucosal resection or an endoscopic submucosal dissection.

22. The method of claim 21, wherein the method comprises:
    dividing the cushion such that hydrogel is retained on the underlying muscularis propria of the organ and the mucosa and the submucosa are removed from the region of the organ.

23. The method of claim 1, wherein the subject is human.

24. The method of claim 1, wherein the organ is in the gastrointestinal tract.

25. The method of claim 24, wherein the organ is selected from duodenum, stomach, small intestine, colon or rectum.

26. The method of claim 1, wherein the method of dissecting comprises endoscopic mucosal resection or endoscopic mucosal dissection.

* * * * *